(12) United States Patent
Yaghi et al.

(10) Patent No.: US 7,652,132 B2
(45) Date of Patent: Jan. 26, 2010

(54) IMPLEMENTATION OF A STRATEGY FOR ACHIEVING EXTRAORDINARY LEVELS OF SURFACE AREA AND POROSITY IN CRYSTALS

(75) Inventors: Omar M. Yaghi, Ann Arbor, MI (US); Adam J. Matzger, Ann Arbor, MI (US); Jesse L. C. Rowsell, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1017 days.

(21) Appl. No.: 10/841,983

(22) Filed: May 7, 2004

(65) Prior Publication Data

US 2004/0225134 A1 Nov. 11, 2004

Related U.S. Application Data

(60) Provisional application No. 60/527,511, filed on Dec. 5, 2003, provisional application No. 60/469,483, filed on May 9, 2003.

(51) Int. Cl.
*C07D 471/22* (2006.01)
*C07F 5/00* (2006.01)
*C07F 3/06* (2006.01)

(52) U.S. Cl. .............. 540/145; 534/15; 556/43; 556/46; 556/51; 556/58; 556/72; 556/89; 556/112; 556/113; 556/136; 556/141

(58) Field of Classification Search .......... 556/43, 556/46, 51, 58, 72, 89, 112, 113, 136, 141, 556/137; 534/15; 540/145
See application file for complete search history.

(56) References Cited

U.S. PATENT DOCUMENTS 3,144,418 A 8/1964 Hill et al.
(Continued)

FOREIGN PATENT DOCUMENTS

CA 2 387 122 2/2001
(Continued)

OTHER PUBLICATIONS

Chen et al., Science, vol. 291, pp. 1021-1022 (2001).*
(Continued)

*Primary Examiner*—Porfirio Nazario Gonzalez
(74) *Attorney, Agent, or Firm*—Brooks Kushman P.C.

(57) ABSTRACT

The present invention provides a metal-organic framework ("MOF") comprising a plurality of metal clusters and a plurality of multidentate linking ligands. Each metal of the plurality of metal clusters comprises one or more metal ions. Each ligand of the plurality of multidentate linking ligands connects adjacent metal clusters. The present invention also provides a method of forming the metal-organic framework. The method of the invention comprises combining a solution comprising one or metal ions with a multidentate linking ligand having a sufficient number of accessible sites for atomic or molecular adsorption that the surface area of the resulting metal-organic framework is greater than 2,900 $m^2/g$.

28 Claims, 8 Drawing Sheets a 2,965 $m^2/g$ b 5,683 $m^2/g$ c 6,200 $m^2/g$ d 7,745 $m^2/g$

U.S. PATENT DOCUMENTS

| | | | |
|---|---|---|---|
| 4,359,327 | A | 11/1982 | Armand et al. |
| 5,629,523 | A | 5/1997 | Ngo et al. |
| 5,648,508 | A | 7/1997 | Yaghi |
| RE35,908 | E | 9/1998 | Kitaguchi et al. |
| 5,862,796 | A | 1/1999 | Seki et al. |
| 5,880,471 | A | 3/1999 | Schelten et al. |
| 5,940,460 | A | 8/1999 | Seidel et al. |
| 6,072,181 | A | 6/2000 | Hassard et al. |
| 6,312,902 | B1 | 11/2001 | Shultz et al. |
| 6,348,607 | B1 | 2/2002 | Müller et al. |
| 6,479,680 | B1 | 11/2002 | Bassler et al. |
| 6,479,826 | B1 | 11/2002 | Klann et al. |
| 6,518,441 | B2 | 2/2003 | Grosch et al. |
| 6,545,281 | B1 | 4/2003 | McGregor et al. |
| 6,617,467 | B1 | 9/2003 | Mueller et al. |
| 6,624,318 | B1* | 9/2003 | Muller et al. ............ 549/529 |
| 6,893,564 | B2* | 5/2005 | Mueller et al. .......... 210/502.1 |
| 6,930,193 | B2 | 8/2005 | Yaghi et al. |
| 6,965,026 | B2 | 11/2005 | Zaworotko et al. |
| 2003/0004364 | A1* | 1/2003 | Yaghi et al. .................. 556/46 |
| 2003/0050487 | A1 | 3/2003 | Muller et al. |
| 2003/0078311 | A1 | 4/2003 | Muller et al. |
| 2003/0148165 | A1 | 8/2003 | Mueller et al. |
| 2003/0222023 | A1 | 12/2003 | Mueller et al. |
| 2004/0081611 | A1 | 4/2004 | Muller et al. |
| 2004/0097724 | A1 | 5/2004 | Muller et al. |
| 2004/0110950 | A1 | 6/2004 | Li et al. |
| 2004/0225134 | A1 | 11/2004 | Yaghi et al. |
| 2004/0265670 | A1 | 12/2004 | Mueller et al. |

FOREIGN PATENT DOCUMENTS

| | | |
|---|---|---|
| CA | 2 414 756 | 1/2003 |
| CA | 2 414 779 | 1/2003 |
| DE | 44 08 772 | 9/1994 |
| DE | 197 23 950 | 12/1998 |
| DE | 198 35 907 | 2/2000 |
| DE | 198 47 629 | 4/2000 |
| DE | 199 36 547 | 2/2001 |
| DE | 100 15 246 | 10/2001 |
| DE | 100 32 884 | 1/2002 |
| DE | 100 32 885 | 1/2002 |
| DE | 101 11 230 | 9/2002 |
| DE | 101 43 195 | 3/2003 |
| EP | 0 557 116 | 8/1993 |
| EP | 0 727 608 | 8/1996 |
| EP | 0 790 253 | 8/1997 |
| EP | 1 280 090 A1 | 1/2003 |
| JP | 2004024247 | 1/2004 |
| WO | WO 97/46711 | 12/1997 |
| WO | WO 99/05151 | 2/1999 |
| WO | WO 00/78837 | 12/2000 |
| WO | WO 01/16209 | 3/2001 |
| WO | WO 01/27186 | 4/2001 |
| WO | WO 02/070526 | 9/2002 |
| WO | WO 02/088148 | 11/2002 |
| WO | WO 03/035717 | 5/2003 |
| WO | WO 03/044228 | 5/2003 |

OTHER PUBLICATIONS

Kaye et al., JACS, vol. 129, No. 46, pp. 14176-14177 (2007).*
Wong-Foy et al., JACS, vol. 128, No. 11, pp. 33494-33495 (2006).*
Millward et al., JACS, vol. 127, No. 51, pp. 17998-17999 (2005).*
Britt et al., PNAS, vol. 105, No. 33, pp. 11623-11627 (2008).*
Dren et al., Langmuir, vol. 20, No. 7, pp. 2683-2689 (2004).*
McGregor, Douglas S. et al., "Semi-Insulating Bulk GaAs Thermal Neutron Imaging Arrays," IEEE Transactions on Nuclear Science, vol. 43, No. 3, Jun. 1996, pp. 1357-1364.
Rose, A., "Sputtered Boron Films on Silicon Surface Barrier Detectors," Nuclear Instruments and Methods, 52, 1967, pp. 166-170.
Feigl, B. et al., "Der Gd-Neutronenzahler," Nuclear Instruments and Methods, 61, Wien, Austria, 1968, pp. 349-356.
Mireshghi, A. et al., "High Efficiency Neutron Sensitive Amorphous Silicon Pixel Detectors," IEEE Transactions on Nuclear Science, vol. 41, No. 4, Aug. 1994, pp. 915-921.
Foulon, F. et al., "Neutron Detectors Made From Chemically Vapour Deposited Semiconductors," Proc. MRS, 487, 1998, pp. 591-596.
Dulloo, A.R. et al., "Radiation Response Testing of Silicon Carbide Semiconductor Neutron Detectors For Monitoring Thermal Neutron Flux," Report 97-9TK1-NUSIC-R1, Westinghouse STC, Pittsburgh, PA, Nov. 18, 1997, pp. 6-1-6-14.
Knoll, Glenn F., Radiation Detection and Measurement, 3rd Ed. John Wiley & Sons, Inc., New York, 2000, Chapter 14, pp. 505-508.
Garber, D.I. et al., "Neutron Cross Sections," 3rd Edition, vol. 11, Curves, Brookhaven National Laboratory, Upton, Jan. 1976, pp. 11-13 & pp. 23-24.
McLane, Victoria et al., "Neutron Cross Sections," vol. 2, Neutron Cross Section Curves, Academic Press, San Diego, CA, 1988, pp. 12-13 & pp. 26-27.
McGregor, Douglas, S.et al., "Thin-Film-Coated Bulk GaAs Detectors for Thermal and Fast Neutron Measurements," Nuclear Instruments and Methods in Physics Research A 466, 2001, pp. 126-141.
http://physics.nist.gov/MajResProj/rfcell/drawings.html.
Schelten, J. et al., "A New Neutron Detector Development Based on Silicon Semiconductor and LiF Converter," Physica B 234-236, 1997, pp. 1084-1086.
Atomnaya Energiya, Soviet Atomic energy, Russian Original, vol. 62, No. 4, Apr. 1987, pp. 316-319.
Allier, C.P., "Micromachined Si-Well Scintillator Pixel Detectors," Chapter 8, 2001, pp. 122-134.
McGregor, Douglas S. et al., "Bulk GaAs-Based Neutron Detectors For Spent Fuel Analysis," Proceedings of ICONE 8, 8th Int'l Conf. on Nuclear Eng., Baltimore, MD, Apr. 2-6, 2000, pp. 1-5.
De Lurgio, Patrick M. et al., "A Neutron Detector To Monitor The Intensity of Transmitted Neutrons For Small-Angle Neutron Scattering Instruments," Elsevier Science B.V., Nuclear Instruments And Methods in Physics Research A 505, 2003, pp. 46-49.
Klann, Raymond T. et al., "Development of Semiconductor Detectors For Fast Neutron Radiography," 15th Int'l. conf. on Applications of Accelerators in Research and Industry, Nov. 2000, pp. 1-4.
Gersch, H.K. et al., "The Effect of Incremental Gamma-Ray Doses and Incremental Neutron Fluences Upon The Performance of Self-Biased 10B-Coated High-Purity Epitaxial GaAs Thermal Neutron Detectors," Nuclear Instruments and Methods in Physics Research A 489, Feb. 12, 2002, pp. 85-98.
McGregor, Douglas S. et al., "Thin-Film-Coated Detectors For Neutron Detection," J. of Korean Assoc. For Radiation Protection, vol. 26, 2001, pp. 167-175.
McGregor, Douglas, S. et al., "Designs For Thin-Film-Coated Semiconductor Thermal Neutron Detectors," University of Michigan, Ann Arbor, Michigan, Nov. 14, 2001, pp. 1-6.
McGregor, Douglas, S. et al., "Design Considerations for Thin Film Coated Semiconductor Thermal Neutron Detectors --I: Basics Regarding Alpha Particle Emitting Neutron Reactive Films," Nuclear Instruments & Methods, A 500, 2003, pp. 272-308.
Puckett, P.R. et al., "Thin Film Processes II," Chapter V-2, J.L. Vossen and W. Kern, Eds., Academic Press, Boston, 1991, pp. 749, 768-770.
Sze, S.M., "VLSI Technology," McGraw-Hill, New York, 1983.
Ruska, W.S., "Microelectronic Processing," McGraw-Hill, New York, 1987.
McGregor, Douglas, S. et al., "Self-Biased Boron-10 Coated High-Purity Epitaxial GaAs Thermal Neutron Detectors," IEEE Transactions on Nuclear Science, vol. 47, No. 4, Aug. 2000, pp. 1364-1370.
Klann, Raymond T. et al., "Development of Coated Gallium Arsenide Neutron Detectors," Conference Record of ICONE-8, 8th International Conf. on Nuclear Eng., Apr. 2-6, 2000, Baltimore, MD, pp. 1-6.
McGregor, Douglas, S. et al., "New Surface Morphology for Low Stress Thin-Film-Coated Thermal Neutron Detectors," IEE Transactions on Nuclear Science, vol. 49, No. 4, Aug. 2002, pp. 1999-2004.
http://www.mems-exchange.org.
McGregor, Douglas S. et al., "Recent Results From Thin-Film-Coated Semiconductor Neutron Detectors," Proceedings of SPIE, vol. 4784, 2002, pp. 164-182.

Chae et al., "A route to high surface area, porosity and inclusion of large molecules in crystals," Nature, 2004, vol. 427, pp. 523-527.

Rosi et al., "Hydrogen Storage in Microporous Metal-Organic Frameworks," Science, vol. 300, pp. 1127-1129.

Eddaoudi, M., J. Kim, J.B. Wachter et al., "Porous Metal-Organic Polyhedra: 25Å Cuboctahedron Constructed from 12 $Cu_2(CO_2)_4$ Paddle-Wheel Building Blocks," J. Am. Chem. Soc., 2001, 123, pp. 4368-4369.

Biradha, K., Y. Hongo & M. Fujita, "Open Square-Grid Coordination Polymers of the Dimension 20×20 Å: Remarkably Stable & Crystalline Solids Even After Guest Removal," Angew. Chem. Int. Ed., 2000, 39, No. 21, pp. 3843-3845.

Li, Hailian, C.E. Davis, T.L. Groy, D.G. Kelley, O.M. Yaghi, "Coordinatively Unsaturated Metal Centers in the Extended Porous Framework of $Zn_3(BDC)_3 \cdot 6CH_3OH$ (BDC=1,4-Benzenedicarboxylate)," J. Am. Chem. Soc. 1998, 120, pp. 2186-2187.

Yaghi, O.M., G. Li, H. Li, "Selective binding and removal of guests in a microporous metal-organic framework," Nature, vol. 378(6558), Dec. 14, 1996, pp. 703-706.

Yaghi, O.M., C.E. Davis, G. Li, and H. Li, "Selective Guest Binding by Tailored Channels in a 3-D Porous Zinc(II)-Benzenetricarboxylate Network," J. Am. Chem. Soc. 1997, 199, pp. 2861-2868.

Yaghi, O.M., H. Li, "Hydrothermal Synthesis of a Metal-Organic Framework Containing Large Rectangular Channels," J. Am. Chem. Soc. 1995, 117, pp. 10401-10402.

Yaghi, O.M., H. Li, C. Davis, D. Richardson and T.L. Groy, "Synthetic Strategies, Structure Patterns, and Emerging Properties in the Chemistry of Modular Porous Solids," Acc. Chem. Res. 1998, 31, pp. 474-484.

Li, H., M. Eddaoudi, D.A. Richardson and O.M. Yaghi, Porous Germanates: Synthesis, Structure, and Inclusion Properties of $Ge_7O_{14.5}F_2 \cdot [(CH_3)_2NH_2]_3(H_2O)_{0.86}$, J. Am. Chem. Soc., 1998, 120, pp. 8567-8568.

Li, H., M. Eddaoudi, T.L. Groy and O.M. Yaghi, Establishing Microporosity in Open Metal—Organic Frameworks: Gas Sorption Isotherms for Zn(BDC) (BDC = 1,4-Benzenedicarboxylate), J. Am Chem. Soc. 1998, 120, pp. 8571-8572.

Li, H. and O.M. Yaghi, "Transformation of Germanium Dioxide to Microporous Germanate 4-Connected Nets," J. Am Chem. Soc. 1998, 120, pp. 10569-10570.

Reineke, T.M., M. Eddaoudi, M. Fehr, D. Kelley and O.M. Yaghi, "From Condensed Lanthanide Coordination Solids to Microporous Frameworks Having Accessible Metal Sites," J. Am. Chem. Soc. 1999, 121, pp. 1651-1657.

Li, H., M. Eddaoudi and O.M. Yaghi, "An Open-Framework Germanate with Polycubane-Like Topology," Angew. Chem. Int. Ed. 1999, 38, No. 5, pp. 653-655.

Reineke, T.M., M. Eddaoudi, M. O'Keeffe and O.M. Yaghi, "A Microporous Lanthanide—Organic Framework," Angew. Chem. Int. Ed. 1999, 38, No. 17, pp. 2590-2594.

Chen, B., M. Eddaoudi, T.M. Reineke, J.W. Kampf, M. O'Keeffe and O.M. Yaghi, $Cu_2(ATC) \cdot 6H_2O$: Design of Open Metal Sites in Porous Metal-Organic Crystals (ATC: 1,3,5,7-Adamantane Tetracarboxylate), J. Am. Chem. Soc. 2000, 122, pp. 11559-11560.

Chae, H.K., M. Eddaoudi, J. Kim, S.I. Hauck, J.F. Hartwig, M. O'Keeffe and O.M. Yaghi, "Tertiary Building Units: Synthesis, Structure, and Porosity of a Metal-Organic Dendrimer Framework (MODF-1)," J. Am. Chem. Soc. 2001, 123, pp. 11482-11483.

Braun, M.E., C.D. Steffek, J. Kim, P.G. Rasmussen and O.M. Yaghi, "1,4-Benzenedicarboxylate derivatives as links in the design of paddle-wheel units and metal-organic frameworks," Chem. Commun., 2001, pp. 2532-2533.

Barton, T.J., L.M. Bull, W.G. Klemperer, D.A. Loy, B. McEnaney, M. Misono, P.A. Monson, G. Pez, G.W. Scherer, J.C. Vartuli and O.M. Yaghi, "Tailored Porous Materials," Chem. Mater. 1999, 11, pp. 2633-2656.

Eddaoudi, M., J. Kim, M. O'Keeffe and O.M. Yaghi, "$Cu_2[o\text{-}Br\text{-}C_6H_3(CO_2)_2]_2(H_2O)_2 \cdot (DMF)_8(H_2O)_2$: A Framework Deliberately Designed To Have the Nbo Structure Type," J. Am. Chem. Soc., 2002, vol. 124, No. 3, pp. 376-377.

Rosi, N.L., M. Eddaoudi, J. Kim, M. O'Keeffe and O.M. Yaghi, "Advances in the chemistry of metal-organic frameworks," CrystEngComm, 2002, 4(68), pp. 401-404.

Plevert, J., R. Sanchez-Smith, T.M. Gentz, H. Li, T.L. Groy, O.M. Yaghi and M. O'Keeffe, "Synthesis and Characterization of Zirconogermanates," Inorganic Chemistry, vol. 42, No. 19, 2003, pp. 5954-5959.

Vodak, D.T., K. Kim, L. Iordanidis, P.G. Rasmussen, A.J. Matzger and O.M. Yaghi, "Computation of Aromatic $C_3N_4$ Networks and Synthesis of the Molecular Precursor $N(C_3N_3)_3Cl_6$," Chem. Eur. J. 2003, 9, pp. 4197-4201.

Olaf Delgado Friedrichs, Michael O'Keeffe and Omar M. Yaghi, "Three-periodic nets and tilings: regular and quasiregular nets," Acat Cryst., 2003, A59, pp. 22-27.

Olaf Delgado Friedrichs, Michael O'Keeffe and Omar M. Yaghi, "Three-periodic nets and tilings: semiregular nets," Acat Cryst., 2003, A59, pp. 515-525.

Hailian Li, Jaheon Kim, Michael O'Keeffe and Omar M. Yaghi, "$[Cd_{16}In_{64}S_{134}]^{44-}$: 31-Å Tetrahedron with a Large Cavity," Angew. Chem. Int. Ed., 2003, 42, pp. 1819-1821.

Chae, H.K., J. Kim, O.D. Friedrichs, M. O'Keeffe and O.M. Yaghi, "Design of Frameworks with Mixed Triangular and Octahedral Building Blocks Exemplified by the Structure of $[Zn_4O(TCA)_2]$ Having the Pyrite Topology," Angew. Chem. Int. Ed, 2003, 42, pp. 3907-3909.

Plevert, J., T.M. Gentz, T.L. Groy, M. O'Keeffe and O.M. Yaghi, "Layered Structures Constructed from New Linkages of $Ge_7(O,OH,F)19$ Clusters," Chem. Mater., 2003, 15, pp. 714-718.

Duren, T., L. Sarkisov, O.M. Yaghi and R.Q. Snurr, "Design of New Materials for Methane Storage," Langmuir, 2004, 20, pp. 2683-2689.

Rowsell, J.L.C., A.R. Millward, K.S. Park and O.M. Yaghi, "Hydrogen Sorption in Functionalized Metal-Organic Frameworks," J. Am. Chem. Soc., 2004, 126, pp. 5666-5667.

Rowsell, J.L.C., O.M. Yaghi, "Metal-organic frameworks: a new class of porous materials," Microporous and Mesoporous Materials 73 (2004), pp. 3-14.

Rosi, N.L., J. Kim, M. Eddaoudi, B. Chen, M. O'Keeffe and O.M. Yaghi, "Rod Packings and Metal-Organic Frameworks Constructed from Rod-Shaped Secondary Building Units," J. Am. Chem. Soc., 2005, 127, pp. 1504-1518.

Chen, B., N.W. Ockwig, F.R. Fronczek, D.S. Contreras and O.M. Yaghi, "Transformation of a Metal-Organic Framework from the NbO to PtS Net," Inorganic Chemistry, vol. 44, No. 2, 2005, pp. 181-183.

U.S. Appl. No. 10/270,642, filed Oct. 16, 2002, Mueller et al.

U.S. Appl. No. 10/611,863, filed Jul. 3, 2003, Mueller et al.

U.S. Appl. No. 10/983,629, filed Nov. 9, 2004, Hesse et al.

Bondi, A., van der Waals Volumes and Radii, Journal of Phys. Chem., Mar. 16, 1964, vol. 68, No. 3, pp. 441-451.

Bennett, J.M. and J.V. Smith, *Positions of Cations and Molecules in Zeiolites with the Faujastie-Type Framework I. Dehydrated Ca-Ex-changed Faujasite*, Mat. Res. Bull., vol. 3., No. 8, pp. 633-642.

Hoskins, B.F. and R. Robson, *Infinite Polymeric Frameworks Consisting of Three Dimensionally Linked Rod-Like Segments*, J. Am. Chem. Soc., 1989, vol. 111, pp. 5962-5964.

Fagan, P.J. and M.D. Ward, *Building Molecular Crystals*, Sci. Am., Jul. 1992, pp. 48-54.

Stein, A., S.W. Keller and T.E. Mallouk, *Turning Down the Heat, Design and Mechanism in Solid-State Synthesis*, Mar. 12, 1993, vol. 259, pp. 1558-1564.

Russell, V.A., C.C. Evans, W.Li and M.D. Ward, *Nanoporous Molecular Sandwiches: Pillard Two-Dimensional Hydrogen-Bonded Networks with Adjustable Porosity*, Science, Apr. 25, 1997, vol. 276, pp. 575-579.

Husing, N. and U. Schubert, *Aerogels-Airy Materials: Chemistry, Structure, and Properties*, Agnew. Chem. Int. Ed., 1998, vol. 37, pp. 22-45.

Menon, V.C. and S. Komarneni, *Porous Adsorbents for Vehicular Natural Gas Storage: A Review*, J. of Porous Materials, 1998, vol. 5, pp. 43-58.

Jones, C.W., K. Tsuji and M.E. Davis, *Organic-Functionalized Molecular Sieves as Shape-Selective Catalysts*, Nature, May 7, 1998, vol. 393, pp. 52-54.

Makoto, F., *Self-Assembly of [2] Catenanes Containing Metals in Their Backbones*, Account of Chemical Research, 1999, vol. 32, No. 1, pp. 53-61.

Li, H., M. Eddaoudi, M. O'Keefe and O.M. Yaghi, *Design and Synthesis of an Exceptionally Stable and Highly Porous Metal-Organic Framework*, Nature, Nov. 18, 1999, vol. 402, pp. 276-279.

Li, H., C.E. Davis, T.L. Groy, D.G. Kelley and O.M. Yaghi, *Coordinately Unsaturated Metal Centers in the Extended Porous Framework of $Zn_3(BDC)_3 6CH_3OH$ (BDC = 1, 4-Benzenedicarboxylate)*, J. Am. Chem. Soc., 1998, vol. 120, pp. 2186-1287.

Kiang, Y.-H, G.B. Gardner, S. Lee, Z. Xu and E.B. Lobkovsky, *Variable Pore Size, Variable Chemical Functionality, and an Example of Reactivity Within PorousPhenylacetylene Silver Salts*, J. Am. Chem. Soc., 1999, vol. 121, pp. 8204-8215.

Eddaoudi, M. , H. Li and O.M. Yaghi, *Highly Porous and Stable Metal—Organic Frameworks: Structure Design and Sorption Properties*, J. Am. Chem. Soc., 2000, vol. 122, pp. 1391-1397.

Noro, S., S. Kitagawa, M. Kondo and K. Seki, *A New, Methane Adsorbent, Porous Coordination Polymer $[\{CuSiF_6(4,4'-bipyridine)_2\}_n]$*, Angew. Chem. Int. Ed., 2000, vol. 39, No. 12, pp. 2081-2084.

Yaghi, O.M., M. O'Keefe and M. Kanatzidis, *Design of Solids from Molecular Building Blocks: Golden Opportunities for Solid State Chemistry*, J. Solid State Chem., 2000, vol. 152, pp. 1-2.

Reineke, T.M., M. Eddaoudi, D. Moler, M. O'Keefe and O.M. Yaghi, *Large Free Volume in Maximally Interpenetrating Networks: The Role of Secondary Building Units Exemplified by $Tb_2(ADB)_3[CH_3]_2 SO]_4 16[(CH_3)_2SO]$*, J. Am. Chem. Soc., 2000, vol. 122, pp. 4843-4844.

Eddaoudi, M., D.B. Moler, H. Li, B. Chen, T.M. Reineke, M. O'Keefe and O.M. Yaghi, *Modular Chemistry: Secondary Building Units as a Basis for the Design of Highly Porous and Robust Metal—Organic Carboxylate Frameworks*, Acc. Chem. Res., 2001, vol. 34, pp. 319-330.

Seki, K., *Design of an Adsorbent with an Ideal Pore Structure for Methane Adsorption Using Metal Complexes*, Chem. Commun., 2001, 1496-1497.

Kim, J., B. Chen, T.M. Reineke, H. Li, M. Eddaoudi, D.B. Moler, M. O'Keefe and O.M. Yaghi, *Assembly of Metal—Organic Frameworks from Large Organic and Inorganic Secondary Buiolding Units: New Examples and Simplifying Principles for Complex Structures*, J. Am. Chem. Soc., 2001, vol. 123, pp. 8239-8274.

Guillou, N., Q. Gao, P.M. Forster, J. Chang, M. Norguè, S. Prk, G. Fèrey and A.K. Cheetham, *Nickel(ii) Phosphate VSB-5: A Magnetic Nanoporous Hydrogenation Catalyst with 24-Ring Tunnels*, Angew. Chem. Int. Ed., 2001,vol. 40, No. 15, pp. 2831-2834.

Naumov, P., G. Jovanovski, M. Ristova, I.A. Razak, S. Cakir, S. Chantraproma, H. Fun and S. Weng Ng, *Coordination of Deprotonated Saccharin in Copper(II) Complexes. Structural Role of the Saccharinate Directed by the Ancillary N-heterocyclic Ligands*, Z. Anorg. Allg. Chem., 2002, vol. 628, pp. 2930-2939.

Wallner, H. and K. Gatterer, *Growth of Pure $Ni(OH)_2$ Single Crystals from Solution—Control of the Crystal Size*, Z. Anorg. Allg. Chem., 2002, vol. 628, pp. 2818-2820.

Patoux, S. and C. Masquelier, *Lithium Insertion into Titanium Phosphates, Silicates and Sulfates*, Chemistry of Materials, 2002, vol. 14, No. 12, pp. 5057-5068.

Nathanial Rosi, Mohamed Eddaoudi, Jaheon Kim et al., "*Infinite Secondary Building Units & Forbidden Catenation in Metal-Organic Frameworks*", Angew. Chem. Int. Ed., 2002, 41, No. 2.

Mohamed Eddaoudi, Jaheon Kim, Nathaniel Rosi et al., "*Systematic Design of Pore Size & Functionality in Isoreticular MOFs & Their Application in Methane Storage*", Science, vol. 295, Jan. 18, 2002.

K. Seki, "*Surface Area Evaluation of Coordination Polymers Having Rectangular Micropores*", Langmuir 2002, 18, pp. 2441-2443.

K. Seki & W. Mori, "*Syntheses & Characterization of Microporous Coordination Polymers with Open Frameworks*", J. Phys. Chem. B, 2002, 106, pp. 1380-1385.

Nathaniel L. Rosi, Juergen Eckert, Mohamed Eddaoudi et al., "*Hydrogen Storage in Microporous Metal-Organic Frameworks*", Science, vol. 300, May 16, 2003, pp. 1127-1129.

Omar Yaghi, Micheal O'Keefe, Nathan W. Ockwig et al., "*Reticular Synthesis and the Design of New Materials*", Nature, vol. 423, Jun. 2003, pp. 705-714.

Chen, B. et al., "Interwoven Metal-Organic Framework of a Periodic Minimal Surface with Extra-Large Pores," Science, v. 291, 2001, pp. 1021-1023.

* cited by examiner

IMPLEMENTATION OF A STRATEGY FOR ACHIEVING EXTRAORDINARY LEVELS OF SURFACE AREA AND POROSITY IN CRYSTALS

CROSS-REFERENCE TO RELATED APPLICATIONS

This application claims the benefit of U.S. Provisional Application Ser. No. 60/527,511 filed Dec. 5, 2003 and of U.S. Provisional Application Ser. No. 60/469,483 filed May 9, 2003. The entire disclosure of each of these applications is hereby incorporated by reference.

STATEMENT REGARDING FEDERALLY SPONSORED RESEARCH OR DEVELOPMENT

The invention was made with Government support under Contract No. 9980469, awarded by The National Science Foundation. The Government has certain rights to the invention.

BACKGROUND OF THE INVENTION

1. Field of the Invention

In at least one embodiment, the present invention relates metal-organic frameworks with high levels of surface area and porosity.

2. Background Art

Porous materials have become important in a number of chemical and physical processes which include, for example, gas/liquid separation, catalysis, luminescence-based sensors, gas storage, and the like. Typically, each specific application requires a tailoring of the pore size and the atomic and molecular adsorption properties to achieve a desired result. One of the outstanding challenges in the field of porous materials is the design and synthesis of chemical structures with exceptionally high surface areas. Until recently the highest surface area for a disordered structure was that of carbon (2,030 m$^2$/g), and for an ordered structures was that of zeolite Y (904 m$^2$/g). More recently crystals of metal-organic frameworks ("MOFs") with similar or somewhat higher surface areas have been reported. Despite this progress and the critical importance of high surface area to many applications involving catalysis, separation and gas storage, no strategy has yet been outlined to answer the question of what the upper limit in surface area for a material is, and how it might be achieved.

Methods for tailoring pore size and adsorption involve altering chemical composition, functionality, and molecular dimensions without changing the underlying topology. (See A. Stein, S. W. Keller and T. E. Mallouk, Science 259, 1558 (1993); and P. J. Fagan and M. D. Ward, Sci. Am. 267, 48 (1992).) Although desirable, few systematic approaches exist because of the lack of control over molecular assembly and in particular, the inability to control the orientation of atomic groups in crystals. These difficulties should be contrasted with the synthesis of organic molecules which can be formed by well characterized and controllable steps. Typically, the insolubility of extended solids requires that assembly of these materials be accomplished in a single step. (See O. M. Yaghi, M. O'Keeffe, and M. Kanatzidis, J. Solid State Chem. 152, 1 (2000).)

Stable, porous metal-organic frameworks have been previously disclosed. Typically, a MOF includes metal clusters linked together in a periodic fashion by linking ligands that increase the distance between the clusters to give a net-like structure. MOFs based on the same net topology (i.e. underlying symmetry and connectivity) are described as "isoreticular". Li et al. disclosed a metal-organic framework (referred to a MOF-5) formed by diffusing triethylamine into a solution of zinc(II) nitrate and benzene-1,4-dicarboxylic acid (H$_2$BDC) in N,N-dimethyl-formamide/chlorobenzene followed by deprotonation of H$_2$BDC and reaction with the Zn$^{2+}$ ions (Li, Hailian, Mohamed Eddaoudi, M. O'Keeffe and O. M. Yaghi, "Design and synthesis of an exceptionally stable and highly porous metal-organic framework," Nature, Vol. 402, pp. 276-279 (Nov. 18 1999)). The MOF-5 framework was found to comprise an extended, porous network having a three-dimensional intersecting channel system with 12.9 Å spacing between centers of adjacent clusters. Although the MOF-5 crystalline structure possesses a number of desirable characteristics, the MOF-5 framework is formed in relatively low yield. Moreover, the MOF-5 structure appears to be limited to a single benzene ring as a linkage between adjacent Zn$_4$(O)O$_{12}$C$_6$ clusters. U.S. Pat. Appl. 20030004364 (the '364 application) expands and enhances the work disclosed in Li et al by providing the preparation for a number of isorecticular metal-organic frameworks. The '364 application recognizes an improvement by requiring that the linking ligand include a phenyl with an attached functional group. It should also be appreciated that the linking ligands in both Li et al and the '364 application are polydentate charged ligands. Although the '364 application provides insight into the tailoring of metal organic frameworks, further improvement is still needed for identifying those molecular components which most effectively increase surface area.

Researchers have also attempted to formulate frameworks having longer links between adjacent clusters by using polytopic N-donor ligands. Synthesis of open frameworks by assembly of metal ions with di-, tri- and polytopic N-donor organic linkers such as 4,4'-bipyridine has produced many cationic framework structures. Although such synthesis may produce frameworks with varying pore sizes, attempts to evacuate/exchange guests within the pores often result in the collapse of the host framework making the practical utility of such frameworks limited.

Accordingly, there is a need in the prior art for porous structures with increased adsorption and in particular, for methods of making such structures in a systematic manner.

SUMMARY OF THE INVENTION

The present invention provides a general strategy that allows the realization of a structure having, by far, the highest surface area reported to date. In one embodiment of the present invention, a metal-organic framework ("MOF") comprising a plurality of metal clusters and a plurality of multidentate linking ligands is provided. The methodology of the present invention represents an enhancement of U.S. Pat. Appl. 20030004364, the entire disclosure of which is hereby incorporated by reference. Each metal of the plurality of metal clusters comprises one or more metal ions. Each ligand of the plurality of multidentate linking ligands connects adjacent metal clusters. The plurality of multidentate linking ligands have a sufficient number of accessible sites for atomic or molecular adsorption that the surface area greater than 2,900 m$^2$/g.

In another embodiment of the invention, the design, synthesis and properties of novel MOF structures and related linking ligands are provided. In this embodiment, crystalline Zn$_4$O(BTB)$_2$ (BTB=1,3,5-benzenetribenzoate), a new metal-organic framework (named MOF-177) with a surface area of 4,500 m$^2$/g is prototyical. MOF-177 combines this exceptional level of surface area with an ordered structure that has extra-large pores capable of binding polycyclic organic guest molecules-attributes heretofore unrealized in one material.

In yet another embodiment of the invention, a method of adsorbing guest species is provided. In this embodiment, a MOF is contacted with a guest species such that at least a portion of the guest species is adsorbed.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

As used herein "linking ligand" means a chemical species (including neutral molecules and ions) that coordinates to two or more metals resulting in an increase in their separation and the definition of void regions or channels in the framework that is produced. Examples include 4,4'-bipyridine (a neutral, multiple N-donor molecule) and benzene-1,4-dicarboxylate (a polycarboxylate anion).

As used herein "non-linking ligand" means a chemical species that is coordinated to a metal but does not act as a linker. The non-linking ligand may still bridge metals, but this is typically through a single coordinating functionality and therefore does not lead to a large separation. Examples include: water, hydroxide, halides, and coordinating solvents such as alcohols, formamides, ethers, nitrites, dimethylsulfoxide, and amines.

As used herein "guest" means any chemical species that resides within the void regions of an open framework solid that is not considered integral to the framework. Examples include: molecules of the solvent that fill the void regions during the synthetic process, other molecules that are exchanged for the solvent such as during immersion (via difflusion) or after evacuation of the solvent molecules, such as gases in a sorption experiment.

As used herein "charge-balancing species" means a charged guest species that balances the charge of the framework. Quite often this species is strongly bound to the framework, i.e. via hydrogen bonds. It may decompose upon evacuation to leave a smaller charged species (see below), or be exchanged for an equivalently charged species, but typically it cannot be removed from the pore of a metal-organic framework without collapse.

As used herein "space-filling agent" means a guest species that fills the void regions of an open framework during synthesis. Materials that exhibit permanent porosity remain intact after removal of the space-filling agent via heating and/or evacuation. Examples include: solvent molecules or molecular charge-balancing species. The latter may decompose upon heating, such that their gaseous products are easily evacuated and a smaller charge-balancing species remains in the pore (i.e. protons). Sometimes space filling agents are referred to as templating agents.

Figure 1:
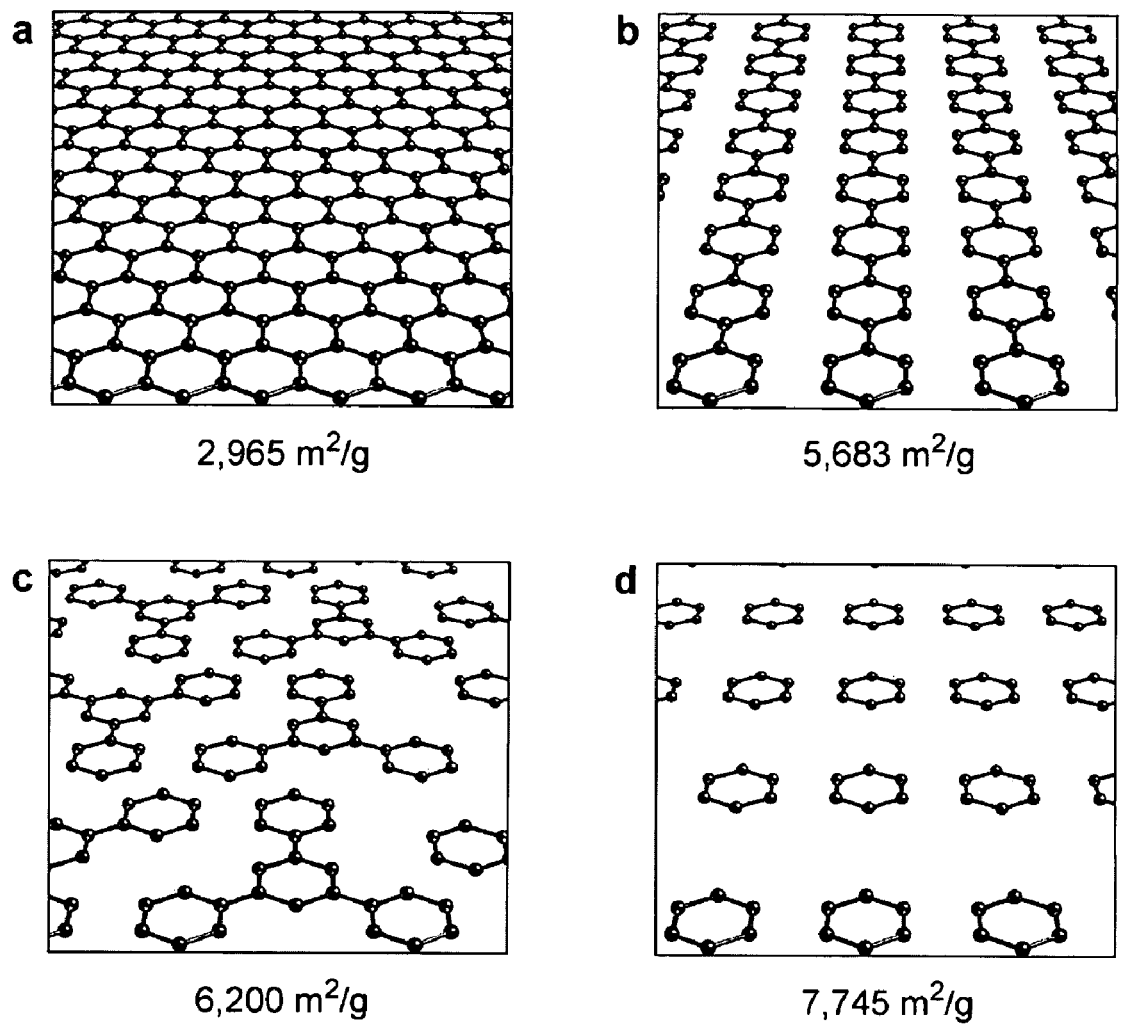
FIG. 1 is an illustration showing the surface area of graphite fragments. (a) A graphene sheet extracted from the graphite structure has a Connolly surface area of 2,965 m$^2$/g when calculated with Cerius modelling software (see Nijkamp, M. G., Raaymakers, J. E., van Dillen, A. J. & de Jong, K. P. Hydrogen storage using physisorption-materials demands. Appl. Phys. A 72, 619-623 (2001)); (b). A series of poly-p-linked 6-membered rings can be extracted from that sheet, thus increasing the surface area to 5,683 m$^2$/g; (c). Excision of 6-membered rings 1,3,5-linked to a central ring raises the surface area to 6,200 m$^2$/g; (d). The surface area reaches a maximum of 7,745 m$^2$/g when the graphene sheet is fully decomposed into isolated 6-membered rings.

The conceptual basis of the present invention can be appreciated by considering a graphene sheet (FIG. 1a). Excision of progressively smaller fragments from this sheet and calculation of their Connolly surface areas (see the Examples) shows that exposing latent edges of the six-membered rings leads to significant enhancement of specific surface area. Thus the surface area of a single infinite sheet is 2,965 m$^2$/g (calculating both sides, see the Examples). For units consisting of infinite chains of poly-p-linked 6-membered rings (FIG. 1b), the surface area is almost doubled (5,683 m$^2$/g). Alternatively, if the graphene sheet is divided into units of three 6-membered rings that are 1,3,5-linked to a central ring (FIG. 1c), the surface area is similarly high (6,200 m$^2$/g). Finally, exposing all latent edges to give isolated six-membered rings (FIG. 1d) leads to an upper limit value of 7,745 m$^2$/g. This analysis does not take into account the hydrogen atoms that would terminate the fragments in MOFs, although that would result in even higher surface areas for those fragments. As set forth below, exposing latent edges serves as a guide for designing structures with exceptional surface areas, and helps to identify the reasons why zeolites are unlikely targets for this objective. Within a typical zeolite structure such as faujasite, guest molecules can only access sorption sites on the walls of the pores leaving the space within each of the sodalite cages, and edges of six-membered M-O-M (M is a metal atom) rings completely inaccessible, which leads to relatively low surface areas. Thus, structures with condensed rings should be avoided in order to maximize exposed ring faces and edges.

In one embodiment, the present invention provides a metal-organic framework comprising a plurality of metal clusters and a plurality of multidentate linking ligands. Each metal of the plurality of metal clusters comprises one or more metal ions. Moreover, the metal cluster may further include one or more non-linking ligands. Each ligand of the plurality of multidentate linking ligands connects adjacent metal clusters. Typically, the plurality of multidentate linking ligands have a sufficient number of accessible sites for atomic or molecular adsorption that the surface area per gram of material is greater than 2,900 m$^2$/g. Specifically, the multidentate ligand has a sufficient number of edges available for atomic or molecular adsorption that the surface area per gram of material is greater than 2,900 m$^2$/g. "Edges" as used herein means a region within the pore volume in proximity to a chemical bond (single-, double-, triple-, aromatic-, or coordination-) where sorption of a guest species may occur. For example, such edges include regions near exposed atom-to-atom bonds in an aromatic or non-aromatic group. Exposed meaning that it is not such a bond that occurs at the position where rings are fused together. Although several methods exist for determining the surface area, a particularly useful method is the Langmuir surface area method. In variations of the invention, the plurality of multidentate linking ligands has a sufficient number of accessible sites (i.e. edges) for atomic or molecular adsorption that the surface area per gram of material is greater than 3,000 m$^2$/g. In other variations, the plurality of multidentate linking ligands has a sufficient number of accessible sites (i.e., edges) for atomic or molecular adsorption that the surface area per gram of material is greater than about 3,500 m$^2$/g. In still other variations, the plurality of multidentate linking ligands has a sufficient number of accessible sites (i.e., edges) for atomic or molecular adsorption that the surface area per gram of material is greater than about 4,000 m$^2$/g. The upper limit to the surface area will typically be about 10,000 m$^2$/g. More typically, upper limit to the surface area will be about 8,000 m$^2$/g.

The metal ions used in the MOFs of the present invention comprise one or more ions selected from the group consisting ions of Group 1 through 16 metals of the IUPAC Periodic Table of the Elements (including actinides and lanthanides). Specific examples of metal ions used in the MOFs of the present invention comprise one or more ions selected from the group consisting Li$^+$, Na$^+$, K$^+$, Rb$^+$, Be$^{2+}$, Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{4+}$, V$^{3+}$, V$^{2+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Co$^{2+}$, Rh$^{2+}$, R$^{30}$, Ir$^{2+}$, Ir$^+$, Ni$^{2+}$, Ni$^+$, Pd$^{2+}$, Pd$^+$, Pt2+, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, Tl$^{3+}$, Si$^{4+}$, Si$^{2+}$, Ge$^{4+}$, Ge$^{2+}$, Sn$^{4+}$, Sn$^{2+}$, Pb$^{4+}$, Pb$^{2+}$, As$^{5+}$, As$^{3+}$, As$^{30}$, Sb$^{5+}$, Sb$^{3+}$, Sb$^+$, Bi$^{5+}$, Bi$^{3+}$, Bi$^+$, and combinations thereof. Of these, Co$^{2+}$, Cu$^{2+}$, and Zn$^{2+}$ are preferred due to their ability to form pre-determined clusters in the synthesis mixture.

A particularly useful metal cluster is described by the formula M$_m$X$_n$ where M is metal ion, X is selected from the group consisting of anions of an non-metal atom of Group 14 through Group 17, m is an integer from 1 to 10, and n is a number selected to charge balance the metal cluster so that the metal cluster has a predetermined electric charge. Examples for the metal ion, M, include Mg$^{2+}$, Ca$^{2+}$, Sr$^{2+}$, Ba$^{2+}$, V$^{2+}$, V$^{3+}$, V$^{4+}$, V$^{5+}$, Mn$^{2+}$, Re$^{2+}$, Fe$^{2+}$, Fe$^{3+}$, Ru$^{3+}$, Ru$^{2+}$, Os$^{2+}$, Co$^{2+}$, Rh$^{2+}$, Ir$^{2+}$, Ni$^{2+}$, Pd$^{2+}$, Pt$^{2+}$, Cu$^{2+}$, Zn$^{2+}$, Cd$^{2+}$, Hg$^{2+}$, Si$^{2+}$, Ge$^{2+}$, Sn$^{2+}$, and Pb$^{2+}$. More specific examples of X are anions of O, N,and S. Accordingly, a representative metal cluster has X as O with n equal to 4 (e.g. Zn$_4$O.)

The MOFs of the present invention may further include a metal cluster that includes one or more non-linking ligands. Useful non-linking ligands include, for example, a ligand selected from the group consisting of O$^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and mixtures thereof.

The MOFs of the present invention also include a multidentate linking ligand. Typically, the multidentate linking ligand will be a charged linking ligand. Such charged linking ligands will include anionic functional groups such as carboxylate (CO$_2^-$), sulfate (SO$_3^-$), and the like. Typically, each of the multidentate linking ligands will include two or more of such charged functional groups. The multidentate ligand may be a bidentate ligand or a tridentate ligand (high numbers of functional groups than three are also within the scope of the invention.) Accordingly, an example of an useful multidentate ligand may contain 2, 3, or more carboxylate groups. The multidentate linking ligand will typically have more than 16 atoms that are incorporated in aromatic rings or non-aromatic rings. In other variations, the multidentate linking ligand has more than 20 atoms that are incorporated in aromatic rings or non-aromatic rings. In each of these variations, the upper limit to the number of atoms incorporated in aromatic or non-aromatic rings is typically about 60 atoms. Alternatively, the multidentate ligand may be described by the number of edge contained in the aromatic or non-aromatic rings. For example, the multidentate ligands typically have at least 16 edges in the aromatic or non-aromatic rings. In other variations, the multidentate ligands typically have at least 18 edges in the aromatic or non-aromatic rings. In still other variations, the multidentate ligands typically have at least 24 edges in the aromatic or non-aromatic rings. In each of these variations, the upper limit to the number of edges in aromatic or non-aromatic rings is typically about 60. A preferred multidentate linking ligand is described by formula I:

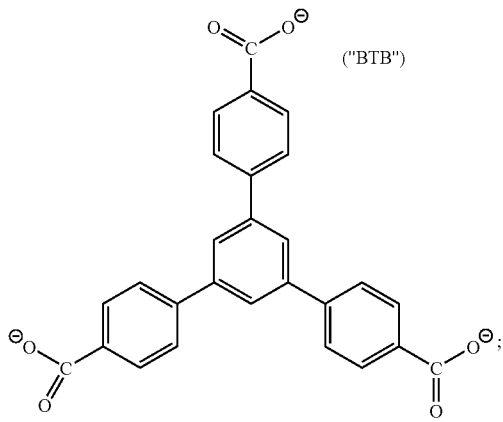

("BTB")

and substituted variations of formula I. Substituted variations will includes components with the hydrogen atoms on the rings replaced by a groups such as an alkyl, an alkoxy, a halogen, nitro, cyano, aryl, aralkyl, and the like. An example of a metal-organic framework of this embodiment has the formula $ZnO_4(BTB)_3*(DEF)_x$ where x represents the number of coordinated N,N-diethylformamide ("DEF") molecules. This number is typically from 0 to about 25.

Another preferred multidentate linking ligand is described by formula II:

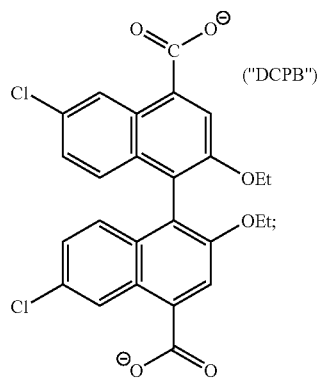

("DCPB")

and substituted variations of formula II. Substituted variations will includes components with the hydrogen atoms on the rings replaced by a groups such as an alkyl, an alkoxy, a halogen, nitro, cyano, aryl, aralkyl, and the like. An example of a metal-organic framework of this embodiment has the formula $ZnO_4(DCBP)_3*(DEF)_x$, where x is an integer representing the number of coordinated diethylformamide molecules. Again, this number is typically from 0 to about 25.

In another embodiment of the present invention, a metal-organic framework is provided. The metal-organic framework of this embodiment comprises a plurality of metal clusters and one or more multidentate linking ligands having formula III:

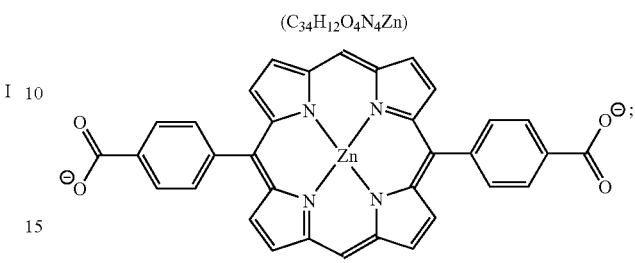

and substituted variations of formula III. Substituted variations will includes components with the hydrogen atoms on the rings replaced by a groups such as an alkyl, an alkoxy, a halogen, nitro, cyano, aryl, aralkyl, and the like. An example of a metal-organic framework of this embodiment has the formula $ZnO_4(C_{34}H_{12}O_4N_4Zn)_3*(DEF)_x$, (also represented as $Zn_4O[Zn(BCPP)]_3*(DEF)_x$) where x represents the number of coordinated N,N-diethylformamide molecules.

In another embodiment of the invention, the metal-organic frameworks set forth above further include a guest species. The presence of such a guest species can advantageously increase the surface area of the metal-organic frameworks. Suitable guest species include, for example, organic molecules with a molecular weight less than 100 g/mol, organic molecules with a molecular weight less than 300 g/mol, organic molecules with a molecular weight less than 600 g/mol, organic molecules with a molecular weight greater than 600 g/mol, organic molecules containing at least one aromatic ring, polycyclic aromatic hydrocarbons, and metal complexes having formula $M_mX_n$ where M is metal ion, X is selected from the group consisting of a Group 14 through Group 17 anion, m is an integer from 1 to 10, and n is a number selected to charge balance the metal cluster so that the metal cluster has a predetermined electric charge; and combinations thereof. The guest species is introduced into the metal-organic framework by contacting the framework with the guest species.

In a variation of this embodiment, the guest species is an adsorbed chemical species. Examples of such species include ammonia, carbon dioxide, carbon monoxide, hydrogen, amines, methane, oxygen, argon, nitrogen, argon, organic dyes, polycyclic organic molecules, and combinations thereof. Again, these chemical species are introduced into the metal-organic framework by contacting the framework with the chemical species.

In another embodiment of the invention, a method of adsorbing a quest species with MOF-5 (a framework with inorganic $[OZn_4]^{6+}$ groups joined to an octahedral array of $[O_2C—C_6H_4—CO_2]^{2-}$ (1,4-benzenedicarboxylate, BDC) groups) or related frameworks is provided. In this method, these frameworks are contacted with the guest species (or chemical species) as set forth above. Related frame works include those frameworks having inorganic $[OZn_4]^{6+}$ groups joined with multidentate ligands that include 1 or 2 substituted or unsubstituted aromatic ring groups (i.e., phenyl, phenylene, mesitylene, etc.)

In a variation of the invention, the metal-organic frameworks set forth above may include an interpenetrating metal-organic framework that increases the surface area of the metal-organic framework. Although the frameworks of the invention may advantageously exclude such interpenetration, there are circumstances when the inclusion of an interpenetrating framework may be used to increase the surface area.

In another embodiment of the present invention, a method of forming a metal-organic framework is provided. The method of this embodiment comprises combining a solution comprising a solvent and one or more ions selected from the group consisting ions of Group 1 through 16 metals of the IUPAC Periodic Table of the Elements (including actinides, and lanthanides) with a multidentate linking ligand. The multidentate ligand is selected such that the surface area of the metal-organic framework has the surface area and adsorption properties set forth above. Examples of metal ions that may be use are selected from the group consisting $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Cr^+$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof. The preferred multidentate linking ligands are the same as those set forth above. Suitable solvents include, for example, ammonia, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, N,N-dimethylformamide, N,N-diethylformamide, and mixtures thereof. In a variation of the this embodiment (without consideration of the absorption properties of the framework), a metal organic framework is formed by combining a solution comprising a solvent and one or more ions selected from the group consisting ions of Group 1 through 16 metals of the IUPAC Periodic Table of the Elements (including actinides, and lanthanides) with a ligand selected from the ligands represented by formulae I, II, or III as set forth above.

The solution utilized in the method of the invention may also include a space-filling agent. Suitable space-filling agents include, for example, a component selected from the group consisting of:

a. alkyl amines and their corresponding alkyl ammonium salts, containing linear, branched, or cyclic aliphatic groups, having from 1 to 20 carbon atoms;

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings;

e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containing linear, branched, or cyclic aliphatic groups, having from 1 to 20 carbon atoms;

h. aryl alcohols having from 1 to 5 phenyl rings;

i. inorganic anions from the group consisting of sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, $O^{2-}$, diphosphate, sulfide, hydrogen sulphate, selenide, selenate; hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and the corresponding acids and salts of said inorganic anions;

j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, trifluoromethylsulfonic acid, N,N-dimethyl formamide, N, N-diethyl formamide, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof. It should be recognized that these space-filling agents can remain within the metal-organic frameworks until removed.

The following examples illustrate the various embodiments of the present invention. Those skilled in the art will recognize many variations that are within the spirit of the present invention and scope of the claims.

Figure 2:
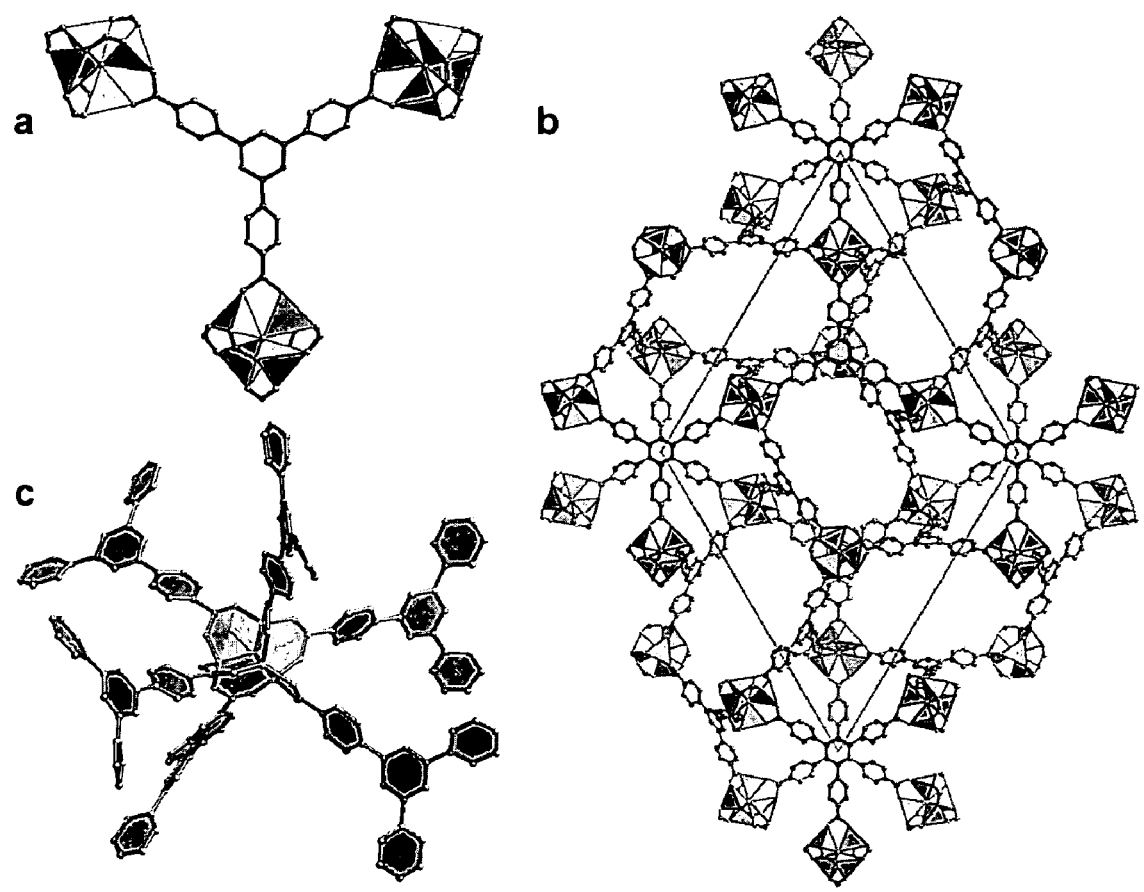
FIG. 2 provides the structure of MOF-177. (a) A BTB unit linked to three OZn$_4$ units (H atoms are omitted). ZnO$_4$ tetrahedra are shown in grey and O, C atoms are shown as light grey and black spheres, respectively. (b) The structure projected down [001] similarly illustrated. For clarity only about half the c axis repeat unit is shown. (c) A fragment of the structure radiating from a central OZn$_4$; six-membered rings are shown as gray hexagons.

These ideas were put into practice by employing established reticular chemistry reactions to link the carboxylate derivative of the type shown in FIG. 1c (BTB, a triangular unit) with basic zinc (II) carboxylate clusters $(Zn_4O(CO_2)_6$, an octahedral unit) (FIG. 2a) into MOF-177. Block-shaped crystals of MOF-177 were produced (see Methods) by heating a mixture of $H_3BTB$ and $Zn(NO_3)_2 \cdot 6H_2O$ in N,N-diethylformamide (DEF) to 100° C. The crystals were formulated by elemental analysis as $Zn_4O(BTB)_2 \cdot (DEF)_{15}(H_2O)_3$ (Anal. Calcd. C, 56.96; H, 7.46; N,7.73. Found: C, 56.90; H, 7.54; N,7.67). An X-ray diffraction study (see Methods and Supporting Information) on a crystal isolated from the reaction mixture confirmed this formulation. It also revealed a remarkably open 3-D structure of $Zn_4O(BTB)_2$ composition, in which each basic zinc acetate cluster is linked to six BTB units (FIG. 2b). In this structure there are 72 exposed edges (48 C—C, 12 C—O, and 12 Zn—O) and only 4 fused edges (Zn—O) per formula unit (FIG. 2c). Remarkably the structure of MOF-177 is entirely constructed of six-membered $C_6H_4$, $C_6H_3$ and $OZn_2CO_2$ rings.

There are two places in the structure maximally far from any framework atom. Positions 0,0,0 and 0,0,1/2, have nearest carbon atom at 7.6 Å and the six positions at 1/2,0,0 etc., have nearest carbon atom at 7.1 Å. Allowing for a carbon atom van der Waals radius of 1.7 Å, these accommodate spheres of diameter 12.8 and 10.8 Å respectively without touching any framework atoms. The latter are connected to produce continuous sinuous channels along 1/2,0,z, 0, 1/2,z, and 1/2,1/2,z (see FIG. 2c). In the as-prepared material, the cavities are occupied by at least 15 DEF and 3 $H_2O$ guests per formula unit. The space occupied by guests alone is 81% of the cell volume. Indeed, gas sorption studies indicate that this space is accessible to incoming guest species and that the framework maintains its integrity in the absence of guests.

Evidence of guest mobility and framework stability initially came from a thermal gravimetric analysis study. A crystalline sample (2.9460 mg) was heated at a constant rate of 5° C./min in air from 25-600° C. Two weight loss steps were observed: the first corresponding to 47.95% occurred between 50 and 100° C., which can be attributed to the loss of guest molecules (calcd. 48.17%), while the second weight loss of 22.01% above 350° C. is due to decomposition of the framework. The lack of any weight loss between 100 and 350° C. indicated that the framework is thermally stable in air at those temperatures. Comparison of the X-ray powder diffraction patterns of the as-synthesized MOF-177 with samples of the material having completely evacuated pores show that the framework periodicity and structure is still preserved, further confirming the architectural stability of the framework in the absence of guests.

Figure 4:
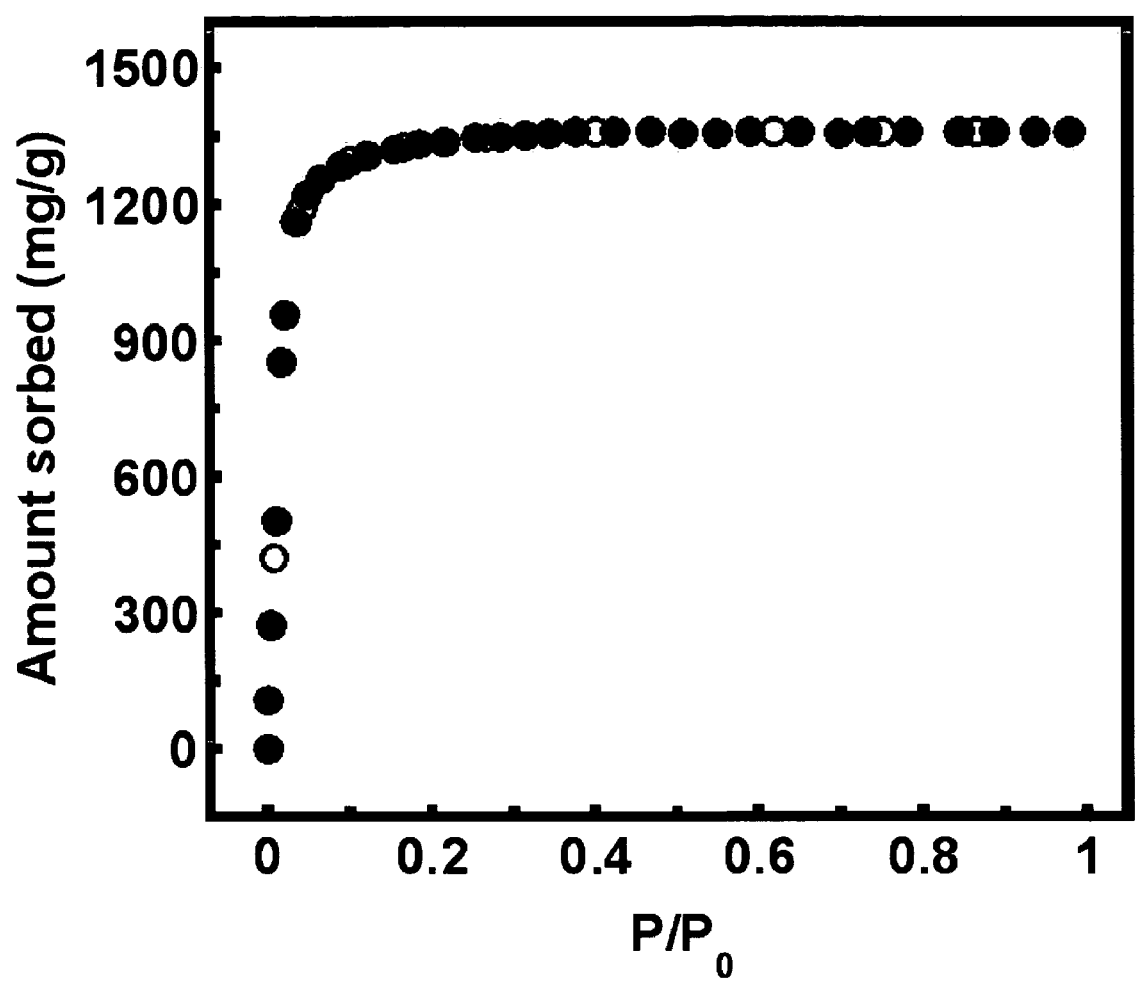
FIG. 4 is a plot of the nitrogen gas sorption isotherm at 78 K for MOF-177 (filled circles, sorption; open circles desorption); P/P$_0$ is the ratio of gas pressure (P) to saturation pressure (P$_0$), with P$_0$=746 torr.

To determine the capacity of this material for gases, the $N_2(g)$ sorption isotherm was measured on samples of MOF-177 where the pores were fully evacuated. The isotherm revealed a reversible type I behavior and showed no hysteresis upon desorption of gas from the pores (FIG. 4). The accessible void space is fully saturated with $N_2$ molecules at relatively low pressures ($P/P_0 \sim 0.2$) with a total weight uptake of 1,288 mg $N_2$ per gram of the fully evacuated framework which correlate to an estimated total number of $N_2$ molecules of 52.7 per formula unit, and 422 per unit cell.

Using the Dubinin-Raduskhvich equation, a pore volume of 1.59 $cm^3/g$ (0.69 $cm^3/cm^3$) was obtained. For monolayer coverage of $N_2$, the apparent Langmuir surface area was found to be 4,500 $m^2/g$. It is worth noting that this surface area is determined with the same level of certainty as that achieved for more established materials and that the pores of MOF-177 are still in the microporous regime (<20 Å-diameter pore size). Nevertheless, the pore volume and surface area of MOF-177 are well beyond those observed for the most porous crystalline zeolites and porous carbon and significantly exceed the previous record for a crystalline MOF material (2,900 $m^2/g$ and 0.59 $cm^3/cm^3$ for MOF-5).

Figure 3:
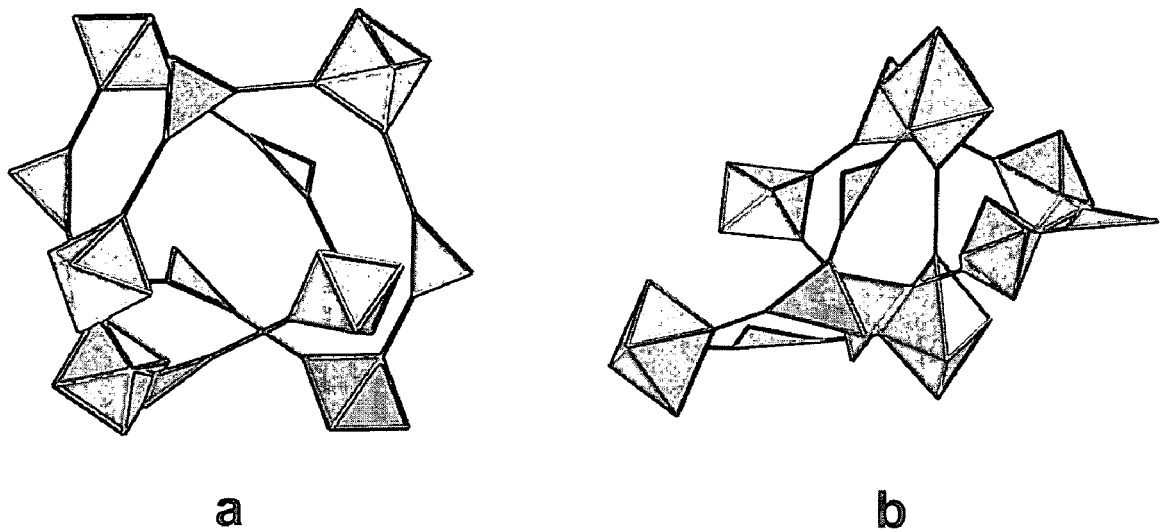
FIG. 3 illustrates the catenation of rings in nets intergrown with their dual structures. The nets are shown augmented with triangles at the 3-coordinated vertices and octahedra at the 6-coordinated vertices. (a) A pair of identical rings in the self-dual pyr net of MOF-150; (b) A six-membered ring of the qom net of MOF-177 catenated with a ring of the dual net. Please notice in the latter that a pairs of 3-coordinated vertices are directly linked as are pairs of 6-coordinated vertices.

The underlying topology of MOF-177 is a (6,3)-coordinated net with the center of the octahedral $OZn_4(CO_2)_6$ cluster as the site of six coordination and the center of the BTB unit the site of 3-coordination. The structure of this net plays an important role in determining pore size by obviating the formation of interpenetrating frameworks as set forth below. The most regular ("default") (6,3)-coordinated net is that named after the pyrite (pyr) structure. However, two such nets can interpenetrate in such a way that all the rings of one structure are penetrated by the links of the other (fully catenated) and vice versa, and indeed MOF-150 based on this topology occurs as an interpenetrating pair of nets (FIG. 3). The second net that fully catenates a given net is said to be the dual of that net and if a net and its dual have the same structure (as in the case of pyr) they are said to be self dual. Although self-duality is a rare property of nets, it does occur also for default structures of nets with 3- 4- and 6-coordination, and thus interpenetration of two (or more) copies of identical nets is found to be a common obstacle to synthesis of large-pore materials.

The present invention provides an effective strategy for avoiding interpenetration (if desired) to utilize nets for which the structure of the dual is very different. The net underlying MOF-177 (FIG. 2b) which is termed qom, is related to the pyr net: in the latter the 6-coordinated sites are arranged as the centers of the spheres in cubic closest packing (i.e. on a face-centered cubic lattice), in qom the corresponding arrangement is that of hexagonal closest packing. However the dual net, although also (6,3)-coordinated, is very different, and as some of the edges link sites of the same coordination (FIG. 3b) it is not a viable candidate for a MOF. Likewise, as qom is very different from its dual, two such qom nets cannot interpenetrate efficiently. Of course the strategy for avoiding the pyr net must be identified in the first place. One may show from simple geometrical arguments that to obviate formation of the pyr net (as in MOF-150), when linking octahedral $OZn_4(CO_2)_6$, one should employ aromatic tricarboxylates such as BTB which is known to have coplanar carboxylates in MOFs.

Given the exceptional stability, porosity, and large pores of MOF-177, the ability to adsorb large organic molecules was tested. Traditionally inclusion in porous materials has been achieved by either in situ synthesis of the guest, synthesis of the framework to entrap the guest or direct incorporation by adsorption. The former two methods are not well suited to making new materials for separations. Furthermore, in all of these methods the use of polycrystalline materials raises the concern that inclusion takes place in inter-crystalline regions rather than directly in the pores. This concern is circumvented by using monocrystalline samples of MOF-177 in all studies. Initial studies demonstrated facile uptake of bromobenzene, 1-bromonaphthalane, 2-bromonaphthalene, and 9-bromoanthracene from solution (see Methods). However, the uniformity of distribution of these guests in the crystals was difficult to determine directly. Accordingly, the inclusion of colored organic molecules in MOF-177 single crystals so that incorporation of the guest could be directly verified visually was evaluated.

Figure 5:
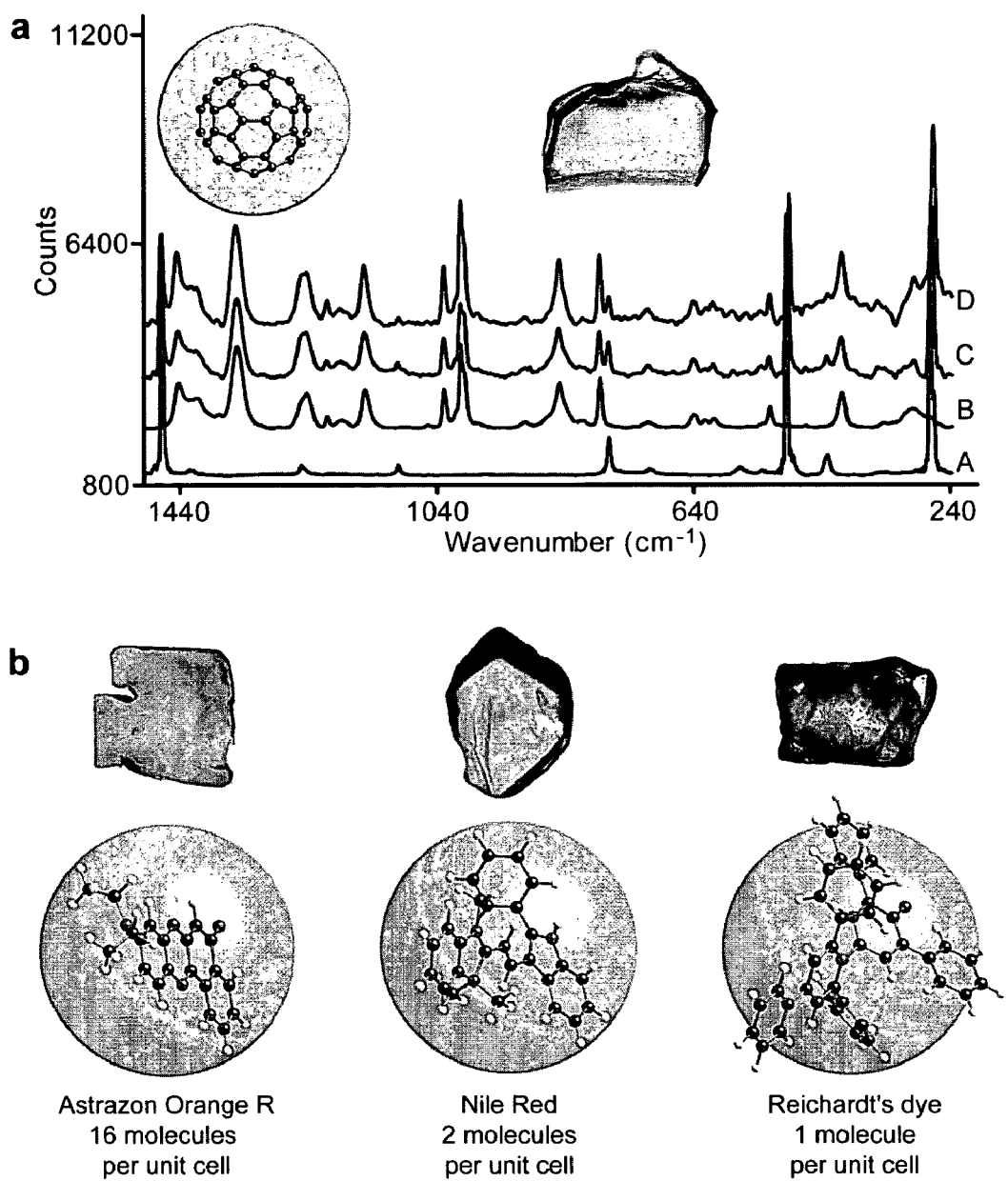
FIG. 5 is an illustration demonstrating the inclusion of polycyclic organic guests. The observation of colorless crystals becoming deep red provided optical evidence for adsorption of C$_{60}$ into MOF-177 single crystals. (a) Analytical evidence was provided by comparison of Raman spectra of a sliced crystal (D) and a whole crystal (C) to bulk C$_{60}$ (A) and an evacuated MOF (B); (b). The ability of MOF-177 crystals to adsorb large guests was quantified for the dyes Astrazon Orange, Nile Red, and Reichardt's dye. These incorporated 16, 2 and 1 molecules per unit cell respectively. Slicing the crystals to expose their inner core proved that for Astrazon Orange and Nile Red, adsorption was uniformly achieved throughout the crystal while for Reichardt's dye, adsorption was primarily restricted to the crystal edges. The ball-and-spoke drawings of the molecules are superimposed on a ball of 11 Å diameter that fits into the pores of MOF-177.

MOF-177 crystals were placed in a $C_{60}$-toluene solution. After several days the crystals' shape and integrity remained intact and a change in color to deep red provided optical evidence of $C_{60}$ inclusion in the framework (FIG. 5a). In order to probe the presence of $C_{60}$, a MOF-177-$C_{60}$ complex was analyzed by Raman spectroscopy. This vibrational spectrum was compared to spectra of bulk $C_{60}$ and to that of evacuated MOF-177. The encapsulated fullerene complex exhibited bands at the same positions as the desolvated MOF-177. However, the fullerene bands were broadened and observed at positions slightly shifted from bulk $C_{60}$ signaling interaction with the framework (FIG. 5a). Uniformity of inclusion was assessed by slicing a single crystal in three parts, thus exposing the inner core, and verifying that the middle portion was evenly colored throughout and that the Raman spectrum exhibited bands for both framework and guest (FIG. 5a).

In order to quantify the ability of MOF-177 to accommodate large polycyclic organic molecules, three dyes, Astrazon Orange R, Nile Red and Reichardt's dye, were selected. Saturated solutions of these compounds were employed to dye the crystals. Examination of a section from the center of the crystal was used to gauge the uniformity of dye distribution (FIG. 5b). In the cases of Astrazon Orange R and Nile Red, the slices were uniformly colored indicating free movement of the dye into the crystals. In the case of Reichardt's dye, this very large molecule only penetrated the outer part of the crystal.

The maximum uptake of these three dyes into MOF-177 was determined as described in the methods section. Astrazon Orange R achieved over 40 wt % in the crystals corresponding to 16 dye molecules in each unit cell. On average, two Nile red molecules entered each unit cell. Reichardt's dye, the largest of the three dyes studied, was the least effective at entering the crystal with only 1 molecule entering each unit cell on average. These results, taken with the diffusion experiments, clearly demonstrate the potential for size selectivity in a regime currently inaccessible with conventional porous materials.

In summary, the present invention provides in one embodiment a general strategy based on exposing edges for achieving ultra-porous crystals having the highest capacity for storage of gases. The importance of utilizing non-self-dual nets in achieving non-interpenetrating structures and thus fully accessible large pores has also been demonstrated. MOF-177 is unique because it combines high surface area with ordered pore structure of extra-large diameter, which, as illustrated for dye inclusion, allows binding of large organic molecules such as petroleum fragments and drug molecules.

Sorption Properties of MOF-5 and Related Frameworks

Sorption properties of MOF-5 (FIG. 6A) in which inorganic $[OZn_4]^{6+}$ groups are joined to an octahedral array of $[O_2C-C_6H_4-CO_2]^{2-}$ (1,4-benzenedicarboxylate, BDC) groups to form a robust and highly porous cubic framework were evaluated. The MOF-5 structure motif and related compounds provide ideal platforms on which to adsorb gases, because the linkers are isolated from each other and accessible from all sides to sorbate molecules. The scaffolding-like nature of MOF-5 and its derivatives leads to extraordinarily high apparent surface areas (2500 to 3000 m²g) for these structures. On a practical level, the preparation of MOFs is simple, inexpensive, and of high yield. For example, the formation reaction for MOF-5 is $4Zn^{2+}+3H_2BDC+8OH^-+3 Zn_4O(BDC)_3 \rightarrow 7H_2O$. The MOF family also has high thermal stability (300° to 400° C.). MOF-5 and isoreticular metalorganic framework-6 (IRMOF-6) (FIG. 6B) outperform other materials in methane adsorption at ambient temperature. Accordingly, the capacity for hydrogen storage was determined.

Hydrogen gas uptake was measured by MOF-5 at 78 K by introducing small amounts of $H_2$ into a chamber containing the guest free form of the material and monitoring the weight change as a function of increasing doses of $H_2$. The measured sorption isotherm shows a type I behavior, in which the saturation is reached at low pressures followed by a pseudoplateau at higher pressure of $H_2$ with a maximum uptake of 13.2 mg of $H_2$ per gram of MOF-5. The observed sharp uptake of $H_2$ at lower pressure indicates favorable sorption interactions between the MOF-5 framework and $H_2$ molecules. It should be appreciated that, similar to the reversible sorption of gases and organic vapors ($N_2$, Ar, $CO_2$, $CHCl_3$, $CCl_4$, $C_6H_6$, and $C_6H_{12}$) in MOF-5, adsorbed $H_2$ molecules can also be reversibly desorbed from the pores by reducing pressure.

Figure 7:
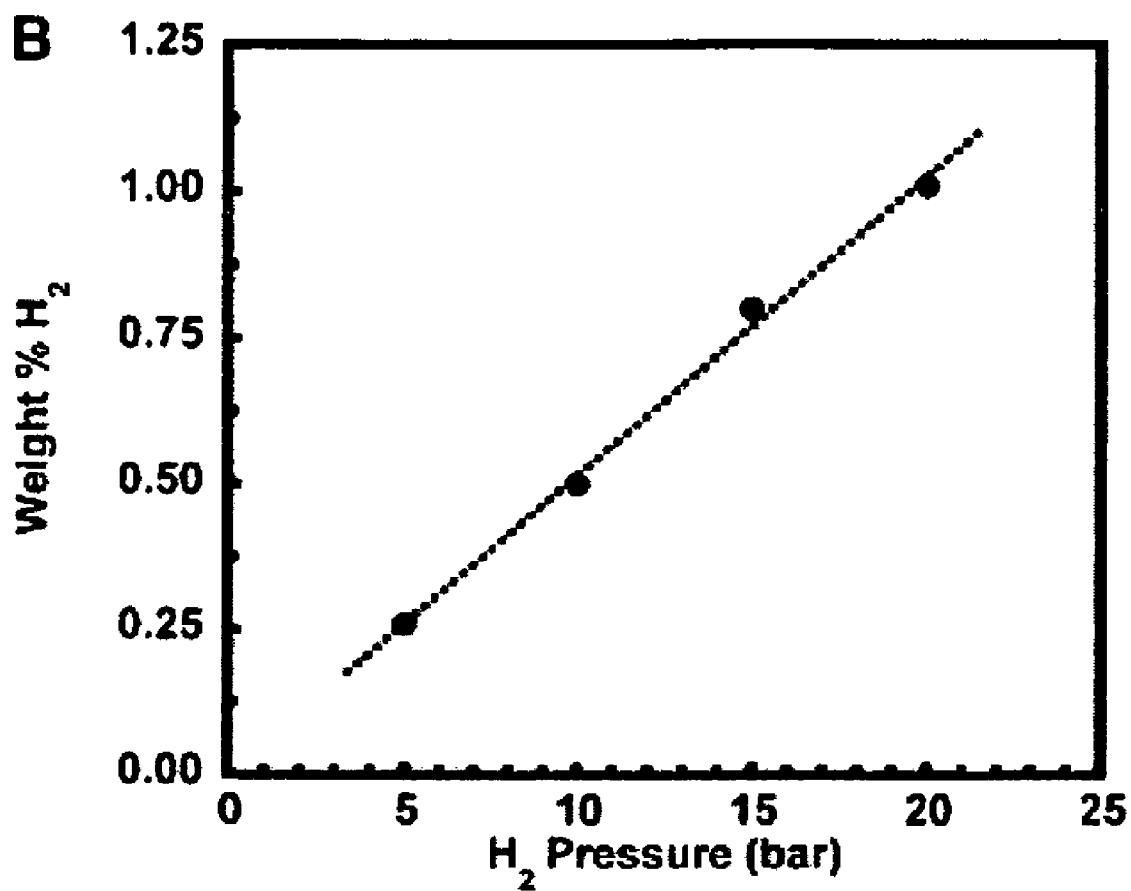
FIG. 7 provides the hydrogen gas sorption isotherm for MOF-5 at 298 K.

$H_2$ sorption was evaluated in conditions that mimic a typical application environment, namely, room temperature and pressures considered safe for mobile fueling. A different sorption apparatus was constructed, in which a 10-g sample of guest-free MOF-5 was charged with $H_2$ up to 20 bar and the weight change monitored as a function of $H_2$ uptake and release. MOF-5 showed substantial $H_2$ uptake that increased linearly with pressure, giving 1.0 weight % at 20 bar (FIG. 7). These findings demonstrate the potential of MOFs for $H_2$ storage applications. The isotherm at ambient temperature is expected to be approximately linear as observed because the material is noticeably undersaturated with $H_2$ in the pressure range explored and, in principle, at higher pressures can take up more $H_2$, up to at least the amount observed at 78 K.

To understand the $H_2$ sorption properties of MOF-5 and hence to potentially control the characteristics of $H_2$ binding, INS spectroscopy of the rotational transitions of the adsorbed hydrogen molecules was performed. Neutrons are scattered inelastically far more strongly by hydrogen than by any other element, which facilitates the observation of rotational tunnel splitting of the librational ground state of the $H_2$ molecule. This splitting is akin to the ortho-para transition for free $H_2$, and this mode is forbidden in optical spectroscopy. This splitting is an extremely sensitive measure of the rotational potential-energy surface, a feature that has made it possible to determine fine details of hydrogen adsorption by INS in a wide variety of materials, including zeolites, nanoporous nickel phosphate VSB-5, and carbon nanotubes.

Figure 8:
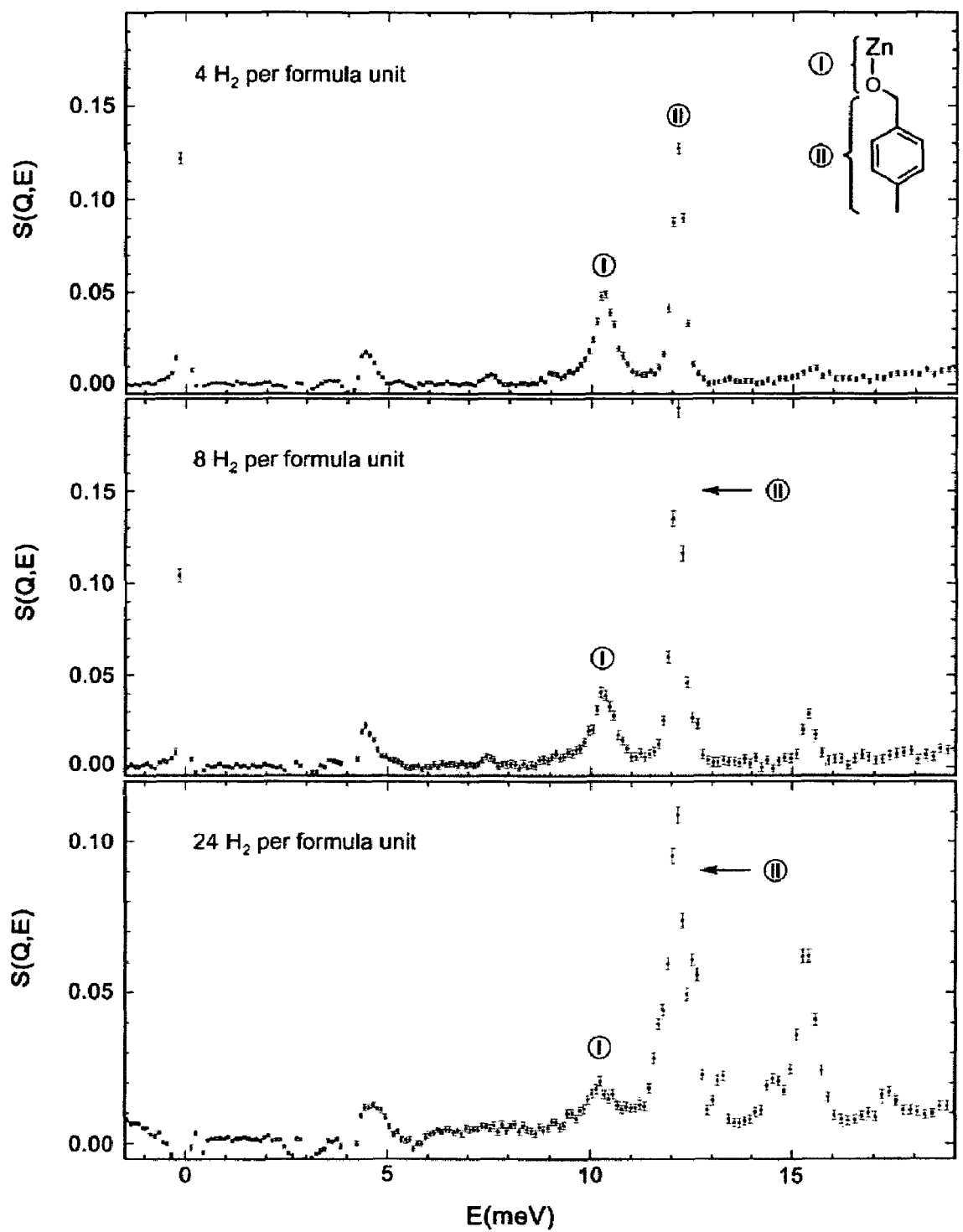
FIG. 8 provides INS spectra (T=10 K) for hydrogen adsorbed in MOF-5 with loadings of 4 H$_2$ (top), 8 H (middle), and 24 H$_2$ (bottom) per formula unit [Zn$_4$O(BDC)$_3$] obtained on the QENS spectrometer at IPNS, Argonne National Laboratory. The spectrum of the guest-free (blank) MOF-5 sample was subtracted in each case. The very slight over subtraction near 4 meV arises from a peak in that region of the blank sample, which cannot be removed by heating under vacuum. Assignments are based on the use of a model potential and observed isotope shifts from a spectrum of D2 in MOF-5. Peaks at 10.3 and 12.1 meV are assigned to the 0-1 transitions for the two principal binding sites (I and II, labeled on the spectra). Other tentative assignments are 4.4 meV (1-2, site II), 15.5 meV (0-2, site II), 7.5 meV (1-2, site I), 17.5 meV (0-2, site I), and 14.5 meV (solid H2). The regions of MOF-5 corresponding to sites I and II are shown schematically in the top right corner.

The INS spectra for MOF-5 are shown in FIG. 8 for three levels of $H_2$ loadings corresponding to 4, 8, and 24 $H_2$ per formula unit. First, the observed peaks are much sharper than those found for $H_2$ in zeolites, VSB-5, and carbon materials. Thus, the adsorption sites for $H_2$ in MOF-5 are well defined compared with those in zeolites, in which the molecule has a variety of binding sites available that are close in energy. Second, the richness of the spectrum immediately leads suggests that more than one type of binding site is present in MOF-5 even though rotational transitions other than 0-1 can be observed. Some progress in assigning peaks can be made with the use of a model for the rotational potential. For reasons of simplicity, the energy eigenvalues for the rotations of $H_2$ with two angular degrees of freedom in a double-minimum potential is used. Thus, the peaks at 10.3 and 12.1 meV can be assigned to the 0-1 transitions for the two sites. These are subsequently referred to as I and II, with the remaining peaks assigned to the 0-2 and 1-2 transitions. These assignments are verified by comparison with the INS spectrum of 4 $D_2$ molecules per formula unit and scaling the rotational energy level diagram by the respective rotational constants of $H_2$ and $D_2$. The rotational barriers associated with sites I and II are found to be 0.40 and 0.24 kcal mol 1, respectively.

Inferences about the nature of the binding sites may also be made from the dependence of the INS spectra on $H_2$ loading. As the average loading is increased from 4 to 8 $H_2$ per formula unit, the intensity of the 12. 1-meV band (site II) roughly doubles, whereas that of the 10.3-meV band (siteI) remains constant. Site I may be associated with Zn and site II with the BDC linkers. Further increases in loading (24 $H_2$ per formula unit) (FIG. 8, bottom panel) show that the line at 12.1 meV splits into four lines, which are associated with four slightly different sites with the BDC linker. This result suggests that further increases in the sorption capacity for these types of materials could be achieved by the use of larger linkers. Indeed, a small peak near 14.5 meV is observed at this high loading corresponding to a small amount of solid $H_2$ (for which the 0-1 transition occurs essentially at the free rotor value of 14.7 meV), indicative of saturation coverage in MOF-5.

The barrier to rotation for the binding site near Zn is somewhat greater than those on the BDC, as one might expect, but also slightly lower than that for the extra-framework $Zn^{2+}$ cation in ZnNaA zeolite, for which the rotational transition was observed at 8 meV. Various factors could contribute to this difference, including different degrees of accessibility of the Zn and the strong electrostatic field in the zeolite supercage. The barriers found for MOF-5 are noticeably higher (0.40 and 0.24 kcal mol 1) than those found in carbons, including single-walled nanotubes, in which it is 0.025 kcal mol 1. Moreover, the rotational band in that case has a width of nearly 2.5 meV compared with 0.5 meV in our case. This value corroborates the much lower mobility (and hence stronger in-teraction) for $H_2$ in MOF-5 than in carbons.

Figure 6:
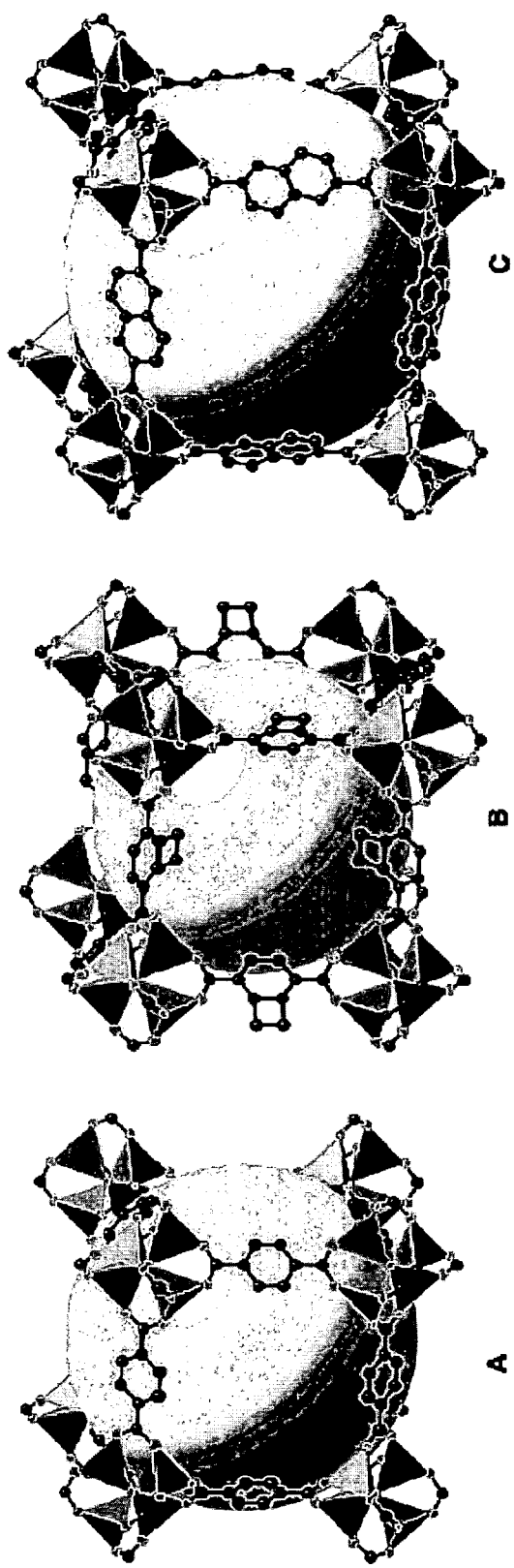
FIG. 6 provides single-crystal x-ray structures of MOF-5 (A), IRMOF-6 (B), and IRMOF-8 (C) illustrated for a single cube fragment of their respective cubic three-dimensional extended structures. On each of the corners is a cluster [OZn$_4$(CO$_2$)$_6$] of an oxygen-centered Zn$_4$ tetrahedron that is bridged by six carboxylates of an organic linker (ZnO$_4$, grey tetrahedron; O, gray spheres; C, black spheres). The large spheres represent the largest spherical volume that would fit in the cavities without intersecting the van der Waals surface of the framework atoms. Hydrogen atoms have been omitted.

The INS results for hydrogen in MOF-5 point to the importance of the organic linkers in determining $H_2$ uptake levels. Accordingly, using the same experimental setup and details outlined above for the room-temperature measurements on MOF-5, $H_2$ sorption in IRMOF-6 and IRMOF-8 was determined (FIG. 6, B and C). Here, the specific $H_2$ uptake is found to approximately doubled and quadrupled, respectively, for IRMOF-6 and -8 relative to that found for MOF-5 at the same (room) temperature and pressure (10 bar). Specifically, for IRMOF-8, the $H_2$ uptake under those conditions is 20 mg of $H_2$ per gram (2.0 weight %)—a capacity well above those found for "active" carbon (0.1 weight %) (CECA, France) and "graphitic" carbon (0.3 weight %). The percent uptake found for MOF-5, IRMOF-6, and IRMOF-8 at room temperature and 10 bar is equivalent to 1.9, 4.2, and 9.1 $H_2$ per formula unit, respectively. The capacity of these structures for hydrogen at room temperature is comparable to the highest capacity achieved for carbon nanotubes at cryogenic temperatures, although the capacity of those materials is very sensitive to preparation conditions and appears to saturate at lower pressures.

METHODS

1. Synthesis

Synthesis of $Zn_4O(BTB)_2.15$ DEF 3 $H_2O$ (MOF-177):

A N,N-diethylformamide (DEF) solution containing 4,4',4"-benzene-1,3,5-triyl-tri benzoic acid ($H_3BTB$; 0.005 g, 1.14× $10^{-5}$ mol) and zinc nitrate hexahydrate $Zn(NO_3)_2.6H_2O$ (0.020 g, 6.72×$10^{-5}$ mol) was placed in a Pyrex tube (10 mm×8 mm o.d. x i.d., 150 mm length). The sealed tube was heated at a rate of 2.0° C./min to 100° C., held at 100° C. for 23 hr, and cooled at a rate of 0.2° C./min to room temperature. Block-shaped yellow crystals of MOF-177 were formed and isolated by washing with DEF (4×2 ml) and drying briefly in the air (ca. 1 min) (0.005 g, 32% based on ligand). Anal. Calcd. for $C_{129}H_{201}N_{15}O_{31}Zn_4 = Zn_4O(BTB)_2 \cdot (15DEF)(3H_2O)$: C, 56.96; H, 7.46; N,7.73. Found: C, 56.90; H, 7.54; N,7.67. FT-IR (KBr, 4000–400 $cm^{-1}$): 1643(s), 1607(s), 1591(s), 1546(m), 1406(vs), 1300(w), 1263(w), 1213(w), 1180(w), 1105(w), 1017(w), 857(w), 809(w), 980(s), 708(w), 669(w).

Synthesis of $Zn_4O(BTB)_2$ (MOF-178):

A 750 mL N,N-dimethylformamide solution of 4,4',4''-benzene-1,3,5-triyl-tri benzoic acid ($H_3BTB$) (3.0 g, 6.8 mmol) and zinc nitrate hexahydrate (18.0 g, 60.5 mmol) was prepared and distributed in 30 equal portions to capped 60 mL glass jars. The vessels were then heated for 16 hr in a 100° C. oven, after which the pale yellow needles of MOF-178 were harvested by filtration and rinsed with N,N-dimethylformamide followed by chloroform. Immersion of the product in chloroform (60 mL) for greater than 3 days, followed by evacuation for 12 hr (25 deg. C., <1 mTorr) yields the activated material $Zn_4O(BTB)_2$ (FW 1154 g/mol, yield 3.2 g, 81%). Similar results were observed when other glass vessels were used. Anhydrous acetonitrile can also be used as the exchange guest, with little effect on the surface area of the final product.

Synthesis of $Zn_4O[ZnX(BCPP)]_3$ (MOF-180):

Zinc nitrate hexahydrate $Zn(NO_3)_2 \cdot 6H_2O$ (3 mg, 0.01001 mmol) was dissolved in 1.2 mL of DMF. 5,15-bis(4-carboxyphenyl) zinc(II) porphyrin ($H_2BCPP$) (1 mg, 0.00164 mmol) was dissolved in 0.2 mL DMF. Both solutions were placed in a tube which was subsequently evacuated/sealed and heated to 105° C. at a rate of 5° C./min and held for 24 hr. The reaction tube was then cooled at a rate of 0.2° C./min. Cubic dark purple crystals of MOF-180 were formed.

Synthesis of $Zn_4O(BBC)_3 \cdot (guest)_x$ (MOF-190)

0.100 g (0.3825 mmol) of zinc nitrate tetrahydrate [$Zn(NO_3)_2 \cdot 4H_2O$] and 0.022 g of 1,3,5-(4'-carboxy-4,4'-biphenyl)benzene (0.033 mmol) was dissolved in 10 ml of N,N-dimethylforamide (DMF) in a 20 scintillation vial and heated to 85° C. for 24 hours. Colorless block-like crystals form on the walls of the vial and are collected mechanically. The topology of MOF-190 is the same as that of MOF-177.

Synthesis of $Zn_4O(C_{26}H_{18}O_4)_3 \cdot (DEF)_{14}(H_2O)_{13.5}$ (IRMOF-17)

S-6,6'-dichloro-2,2'-diethoxy-1,1'-binaphthalene-4,4'-dicarboxylate (DCBP) (21 mg; 0.044 mmol) and $Zn(NO_3)_2 \cdot 4H_2O$ (46 mg; 0.176 mmol) were dissolved in DEF (4 mL) in a 20 mL scintillation vial. Colorless cubic crystals (10 mg; 0.003 mmol; 20%) formed after heating the mixture at 100° C. for 24 h. Anal. Calcd. (%) for $Zn_4O(DCBP)_3 \cdot (DEF)_{14}(H_2O)_{13.5}$: C, 51.84; H, 6.91; N,5.72. Found: C, 51.56; H, 6.07; N,5.73. FT-IR (KBr 4000-500 $cm^{-1}$): 3446(br), 3102(w), 3071(w), 2980(m), 2937(w), 2881(w), 1667(s), 1646(s), 1572(s), 1495(w), 1447(m), 1400(m), 1321(m), 1263(m), 1222(m), 1118(m), 1087(m), 909(w), 826(w), 801(w), 766(w), 511(w). Anal. Calcd. (%) for $Zn_4O(C_{26}H_{18}O_4)_3 \cdot (DEF)_{0.75}(H_2O)_{10}$ (chlorobenzene exchange product): C, 48.48; H, 4.09; N,0.52. Found: C, 48.35; H, 3.01; N,0.62.

2. Surface Area Calculations

The surface areas for graphite, faujasite, and fragments of these structures were obtained via the Connolly Surface method, as implemented by Cerius program.

3. Crystallographic Studies on MOF-177

Crystal (0.30×0.30×0.28 $mm^3$) of $Zn_4O(BTB)_2 \cdot (DEF)_{15} \cdot (H_2O)_3$ was sealed in a glass capillary and mounted on a Bruker SMART APEX CCD diffractometer equipped with a normal focus Mo-target X-ray tube ($\lambda$=0.71073 Å) operated at 2000 W power (50 kV, 40 mA). The X-ray intensities were measured at 273(2) K. A total of 1800 frames were collected with a scan width of 0.3° in ω with an exposure time of 30 s/frame. The frames were integrated with the SAINT software package with a narrow frame algorithm. The integration of the data using trigonal unit cell yielded a total of 173,392 reflections to a maximum 2θ value of 41.68° of which 12,530 were independent and 5233 were greater than 2σ(I). The final cell constants were refined with 5049 reflections with 4.395<2θ<41.661. Analysis of the data showed negligible decay during data collection. Absorption correction was applied by using SADABS. The structure was solved by direct methods and the subsequent difference Fourier syntheses and refined with the SHELXTL (version 6.10) software package, using the trigonal space group P$\bar{3}$1c (No. 163), a=37.072 (2) Å, c=30.033 (2) Å with Z=8 for the formula based on the elemental analysis. There were two independent $Zn_4O$ clusters centred at Wyckoff positions, 2 d and 6 h; the first of these was disordered over two possible orientations. Final full matrix least-squares refinement on $F^2$ converged to R1=0.1538 (F>4σ(F)) and wR2=0.4639 (all data) with GOF=1.397. Additional details are presented as Supporting Information.

4. Diffusion of Bromoarenes

The crystals were transferred from their mother liquor (DMF) to heptane. After 30 minutes, the heptane was removed and fresh heptane was once again added. This process was repeated three times in order to ensure complete displacement of DMF molecules from the porous framework. The excess heptane was then removed and 1 mL of a heptane solution containing 0.007 M of each of the four bromoarenes was added. The crystals remained immersed in this solution for 90 minutes. The concentration of each bromoarene in the supernatant liquid was monitored via gas chromatography. Disappearance of material indicates adsorption of bromoarenes by MOF-177 crystals.

5. Quantification of Dye Uptake

MOF-177 crystals (3-5 mg) were placed in 0.15 mL of a saturated solution of dye in $CH_2Cl_2$. During a period of six days, the supernatant solution was removed and replaced with fresh dye solution twenty times. After the sixth day of inclusion, the crystals were removed from solution and rinsed three times with $CH_2Cl_2$. Individual crystals were precisely weighed with a microgram balance and digested in 40 to 60 μL of 0.1 N NaOH in methanol. This solution was quantitatively transferred to a 2 mL volumetric flask and methanol was added to obtain precise dilution. UV-vis absorbance analysis of the resulting solutions allowed for determination of the concentrations of the dyes and thus for the amount of dye included in the MOF-177 framework.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed:

1. A metal-organic framework (MOF) comprising:
 a plurality of metal clusters, each metal cluster comprising one or more metal ions; and
 a plurality of charged multidentate linking ligands that connects adjacent metal clusters, the plurality of multidentate linking ligands having a sufficient number of accessible sites for atomic or molecular adsorption such that the surface area of the metal-organic framework is greater than about 3,500 m²/g wherein the multidentate linking ligand has more than 16 atoms which are incorporated in aromatic rings or non-aromatic rings.

2. The metal-organic framework of claim 1 further comprising at least one non-linking ligand.

3. The metal-organic framework of claim 1 wherein each metal cluster comprises 3 or more metal ions.

4. The metal-organic framework of claim 1 wherein the plurality of multidentate linking ligands have a sufficient number of accessible sites for atomic or molecular adsorption that the surface area is greater than about 4,000 m²/g.

5. The metal-organic framework of claim 1 wherein each ligand of the plurality of multidentate ligand includes 2 or more carboxylates.

6. The metal-organic framework of claim 1 wherein the metal ion selected from the group consisting Group 1 through 16 metals of the IUPAC Periodic Table of the Elements including actinides, and lanthanides, and combinations thereof.

7. The metal-organic framework of claim 1 wherein the metal ion selected from the group consisting of $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^+$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $AG^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof.

8. The metal-organic framework of claim 1 wherein the metal cluster has formula $M_mX_n$ where M is metal ion, X is selected from the group consisting of a Group 14 through Group 17 anion, m is an integer from 1 to 10, and n is a number selected to charge balance the metal cluster so that the metal cluster has a predetermined electric charge.

9. The metal-organic framework of claim 8 wherein X is selected from the group consisting of O, N, and S.

10. The metal-organic framework of claim 8 wherein X is O and m is 4.

11. The metal-organic framework of claim 8 wherein M is selected from the group consisting of $Mg^{2+}$, $Ca^{2+}$, $Sr^{2+}$, $Ba^{2+}$, $V^{2+}$, $V^{3+}$, $V^{4+}$, $V^{5+}$, $Mn^{2+}$, $Re^{2+}$, $Fe^{2+}$, $Fe^{3+}$, $Ru^{3+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Zn^{2+}$, $Cd^{2+}$, $Hg^{2+}$, $Si^{2+}$, $Ge^{2+}$, $Sn^{2+}$, and $Pb^{2+}$.

12. The metal-organic framework of claim 8 wherein the metal cluster has formula $Zn_4O$.

13. The metal-organic framework of claim 1 wherein the non-linking ligand is selected from the group consisting of $O^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and mixtures thereof.

14. The metal-organic framework of claim 1 further comprising a guest species.

15. The metal-organic framework of claim 14 wherein the guest species increase the surface area of the metal-organic framework.

16. The metal-organic framework of claim 14 wherein the guest species is selected from the group consisting of organic molecules with a molecular weight less than 100 g/mol, organic molecules with a molecular weight less than 300 g/mol, organic molecules with a molecular weight less than 600 g/mol, organic molecules with a molecular weight greater than 600 g/mol, organic molecules containing at least one aromatic ring, polycyclic aromatic hydrocarbons, and metal complexes having formula $M_mX_n$ where M is metal ion, X is selected from the group consisting of a Group 14 through Group 17 anion, m is an integer from 1 to 10, and n is a number selected to charge balance the metal cluster so that the metal cluster has a predetermined electric charge; and combinations thereof.

17. The metal-organic framework of claim 1 further comprising an interpenetrating metal-organic framework that increases the surface area of the metal-organic framework.

18. The metal-organic framework of claim 1 wherein the multidentate linking ligand has more than 20 atoms which are incorporated in aromatic rings or non-aromatic rings.

19. The metal-organic framework of claim 1 further comprising an adsorbed chemical species.

20. The metal-organic framework of claim 1 wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

21. A metal-organic framework (MOF) comprising:
a plurality of metal clusters, each metal cluster comprising one or more metal ions; and
at least one multidentate linking ligand having formula II:

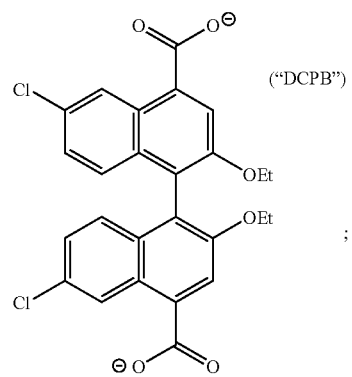

("DCPB")

II or substituted variations of formula II.

22. A metal-organic framework (MOF) comprising:
a plurality of metal clusters, each metal cluster comprising one or more metal ions; and
at least one multidentate linking ligand having formula III:

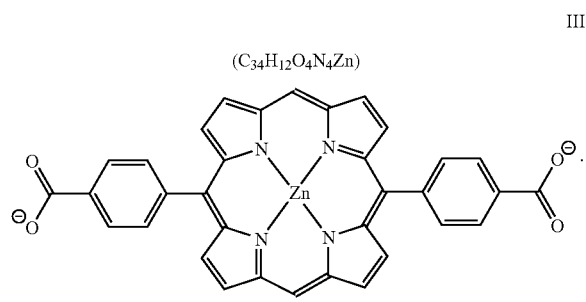

III ($C_{34}H_{12}O_4N_4Zn$)

or substituted variations of formula III.

23. A method of forming a metal-organic framework (MOF), the method comprising:
combining a solution comprising a solvent and metal ions selected from the group consisting Group 1 through 16 metals including actinides, and lanthanides, and combinations thereof with a multidentate linking ligand, the multidentate ligand selected such that the surface area of the metal-organic framework is greater than 3,500 m²/g, wherein the multidentate ligand is selected from from the group consisting of:

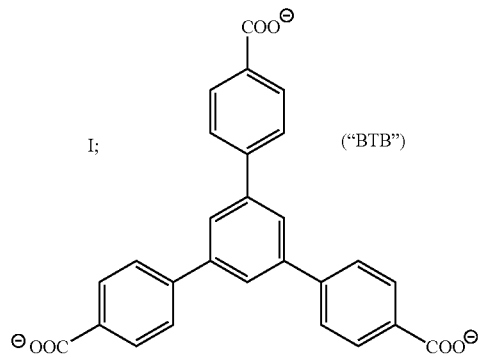

I; ("BTB")

or substituted variations of formula I;

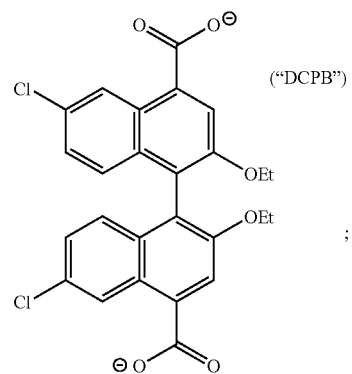

II ("DCPB")

or substituted variations of formula II.

24. The method of claim 23 wherein the solvent comprises a component selected from ammonia, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, N,N-dimethyl formamide, N,N-diethyl formamide, methanol, ethanol, propanol, alcohols, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof.

25. The method of claim 23 wherein the solution further comprises a space-filling agent.

26. The method of claim 23 wherein the space-filling agent is selected from the group consisting of:
a. alkyl amines and their corresponding alkyl ammonium salts, containing linear, branched, or cyclic aliphatic groups, having from 1 to 20 carbon atoms;
b. aryl amines and their corresponding aryl ammonium salts having from 1 to 5 phenyl rings;
c. alkyl phosphonium salts, containing linear, branched, or cyclic aliphatic groups, having from 1 to 20 carbon atoms;
d. aryl phosphonium salts, having from 1 to 5 phenyl rings,
e. alkyl organic acids and their corresponding salts, containing linear, branched, or cyclic aliphatic groups, having from 1 to 20 carbon atoms;
f. aryl organic acids and their corresponding salts, having from 1 to 5 phenyl rings;
g. aliphatic alcohols, containing linear, branched, or cyclic aliphatic groups, having from 1 to 20 carbon atoms;
h. aryl alcohols having from 1 to 5 phenyl rings;
i. inorganic anions from the group consisting of sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, $O^{2-}$, diphosphate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and the corresponding acids and salts of said inorganic anions;
j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, trifluoromethylsulfonic acid, N,N-dimethyl formamide, N,N-diethyl formamide, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof.

27. The method of claim 23 further comprising contacting the metal organic framework with a guest species such that the guest species becomes at least partially incorporated within the metal organic framework.

28. A method of forming a metal-organic framework (MOF), the method comprising:
combining a solution comprising a solvent and metal ions selected from the group consisting of Group 1 through 16 metals of the IUPAC Periodic Table of the Elements with a multidentate linking ligand having formula III:

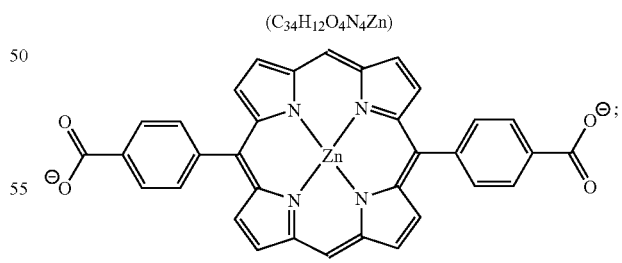

III ($C_{34}H_{12}O_4N_4Zn$)

or substituted variations of formula I.

* * * * *

UNITED STATES PATENT AND TRADEMARK OFFICE
CERTIFICATE OF CORRECTION

PATENT NO. : 7,652,132 B2  Page 1 of 1
APPLICATION NO. : 10/841983
DATED : January 26, 2010
INVENTOR(S) : Omar M. Yughi et al.

It is certified that error appears in the above-identified patent and that said Letters Patent is hereby corrected as shown below:

Column 17, Line 27, Claim 7:

After "$Cu^+$" and before "$Au^+$" delete "$AG^+$" and insert -- $Ag^+$ --.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,652,132 B2
APPLICATION NO. : 10/841983
DATED : January 26, 2010
INVENTOR(S) : Yaghi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1257 days.

Signed and Sealed this

Twenty-eighth Day of December, 2010

David J. Kappos
*Director of the United States Patent and Trademark Office*